US012685494B2

(12) United States Patent
Davidson et al.

(10) Patent No.: US 12,685,494 B2
(45) Date of Patent: Jul. 21, 2026

(54) VOICE COMMUNICATION DEVICE HAVING LOCATING AND PAIRING AND OTHER IMPROVED BADGE FUNCTIONALITY

(71) Applicant: Hill-Rom Services, Inc., Batesville, IN (US)

(72) Inventors: Frederick Collin Davidson, Apex, NC (US); Brandon M. Ayers, Carrboro, NC (US); Mark F. Hettig, Denver, CO (US); Kiana M. Dezelon, Batesville, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 7 days.

(21) Appl. No.: 19/078,457

(22) Filed: Mar. 13, 2025

(65) Prior Publication Data

US 2025/0288259 A1 Sep. 18, 2025

Related U.S. Application Data

(60) Provisional application No. 63/764,945, filed on Feb. 28, 2025, provisional application No. 63/565,642, filed on Mar. 15, 2024.

(51) Int. Cl.
*A61B 5/00* (2006.01)
*A61B 5/11* (2006.01)
(Continued)

(52) U.S. Cl.
CPC ............ *A61B 5/747* (2013.01); *A61B 5/1117* (2013.01); *A61B 5/7435* (2013.01); *A61B 5/749* (2013.01);
(Continued)

(58) Field of Classification Search
CPC ..... A61B 5/1117; A61B 5/7435; A61B 5/747; A61B 5/749; A61G 7/018; G08B 26/008; H04W 4/029; H04W 4/80
See application file for complete search history.

(56) References Cited

U.S. PATENT DOCUMENTS

| | | | |
|---|---|---|---|
| 5,561,412 A | 10/1996 | Novak et al. | |
| 5,838,223 A | 11/1998 | Gallant et al. | |

(Continued)

FOREIGN PATENT DOCUMENTS

| | | |
|---|---|---|
| GB | 2593131 A | 9/2021 |
| JP | 2021502219 A | 1/2021 |

(Continued)

OTHER PUBLICATIONS

Notification of Transmittal of the International Search Report and the Written Opinion of the International Searching Authority, or the Declaration; mailed by the United States Patent and Trademark Office on Jun. 3, 2025, for PCT Patent Application No. PCT/US2025/019530 (13 pages).

(Continued)

*Primary Examiner* — Omer S Khan
(74) *Attorney, Agent, or Firm* — Barnes & Thornburg LLP

(57) ABSTRACT

A healthcare communication system includes a voice communication badge to be worn or otherwise transported by a caregiver. The voice communication badge has a display, a microphone, buttons that are used to select or alter first information appearing on the display, and circuitry including a wireless fidelity (WiFi) module configured to (i) send and receive long range wireless signals to and from one or more of the wireless access points, and (ii) send and receive short range wireless signals. The circuitry also includes a location module to emit beacon signals that are received by at least one receiver of a real-time locating system which includes a (Continued)

Place & receive calls or broadcasts
Users | Roles | Teams
Receive and respond to alerts
Use assignments locating computer that determines a location of the voice communication badge based on the beacon signals.

17 Claims, 8 Drawing Sheets

(51) Int. Cl.

| | |
|---|---|
| *A61G 7/018* | (2006.01) |
| *G08B 26/00* | (2006.01) |
| *H04W 4/029* | (2018.01) |

(52) U.S. Cl.
CPC ........... *A61G 7/018* (2013.01); *G08B 26/008* (2013.01); *H04W 4/029* (2018.02)

(56) References Cited

U.S. PATENT DOCUMENTS

| | | | |
|---|---|---|---|
| 6,892,083 | B2 | 5/2005 | Shostak |
| 6,901,255 | B2 | 5/2005 | Shostak |
| 6,972,683 | B2 | 12/2005 | Lestienne et al. |
| 7,190,802 | B2 | 3/2007 | Rains et al. |
| 7,206,594 | B2 | 4/2007 | Shostak |
| 7,248,881 | B2 | 7/2007 | Shostak |
| 7,257,415 | B2 | 8/2007 | Shostak |
| 7,310,541 | B2 | 12/2007 | Shostak |
| 7,319,386 | B2 | 1/2008 | Collins, Jr. et al. |
| 7,457,751 | B2 | 11/2008 | Shostak |
| 7,538,659 | B2 | 5/2009 | Ulrich et al. |
| 7,764,972 | B2 | 7/2010 | Shostak |
| 7,953,447 | B2 | 5/2011 | Shostak |
| 7,974,924 | B2 | 7/2011 | Holla et al. |
| 7,978,619 | B2 | 7/2011 | Nielsen |
| 8,046,625 | B2 | 10/2011 | Ferguson et al. |
| 8,098,806 | B2 | 1/2012 | Shostak |
| 8,121,649 | B2 | 2/2012 | Shostak |
| 8,169,304 | B2 | 5/2012 | Schuman, Sr. et al. |
| 8,175,887 | B2 | 5/2012 | Shostak |
| 8,260,709 | B2 | 9/2012 | Holla et al. |
| 8,384,526 | B2 | 2/2013 | Schuman, Sr. et al. |
| 8,396,803 | B1 | 3/2013 | Dala et al. |
| D679,673 | S | 4/2013 | Wheaton et al. |
| 8,498,865 | B1 | 7/2013 | Shostak |
| 8,598,995 | B2 | 12/2013 | Schuman et al. |
| 8,626,246 | B2 | 1/2014 | Shostak |
| 8,779,924 | B2 | 7/2014 | Pesot et al. |
| 8,849,718 | B2 | 9/2014 | Dala et al. |
| 8,977,548 | B2 | 3/2015 | Shostak |
| 9,215,583 | B2 | 12/2015 | Shostak |
| 9,504,425 | B2 | 11/2016 | Jooste |
| 9,811,992 | B1 | 11/2017 | Neuvirth-Telem et al. |
| 9,817,809 | B2 | 11/2017 | Shostak |
| 9,866,507 | B2 | 1/2018 | Frenkel et al. |
| 9,892,732 | B1 | 2/2018 | Tian et al. |
| 9,907,473 | B2 | 3/2018 | Tran |
| 10,095,833 | B2 | 10/2018 | Balram et al. |
| 10,257,277 | B2 | 4/2019 | Schlapfer et al. |

| | | | |
|---|---|---|---|
| 10,517,784 | B2 | 12/2019 | Zerhusen et al. |
| D879,061 | S | 3/2020 | Jiang et al. |
| 10,621,980 | B2 | 4/2020 | Kim |
| 10,623,498 | B2 | 4/2020 | Schlapfer et al. |
| 10,884,096 | B2 | 1/2021 | Baek et al. |
| 10,925,551 | B2 | 2/2021 | Hays et al. |
| 10,949,633 | B1 | 3/2021 | Farrell |
| 10,957,445 | B2 | 3/2021 | Faulks et al. |
| 11,024,311 | B2 | 6/2021 | Mixter et al. |
| 11,062,707 | B2 | 7/2021 | Judy et al. |
| 11,152,111 | B2 | 10/2021 | Pipher et al. |
| 11,191,470 | B2 | 12/2021 | Kaib et al. |
| 11,200,897 | B2 | 12/2021 | Yi et al. |
| 11,257,588 | B2 | 2/2022 | Faulks et al. |
| 11,289,194 | B1 | 3/2022 | Pipher et al. |
| 11,302,338 | B2 | 4/2022 | Bechtel et al. |
| 11,317,246 | B1 | 4/2022 | Pipher et al. |
| 11,662,218 | B2 | 5/2023 | Johnson |
| 11,697,301 | B2 | 7/2023 | Moshiri et al. |
| 12,114,974 | B2 | 10/2024 | Al-Ali et al. |
| 2004/0043797 | A1 | 3/2004 | Shostak |
| 2016/0307429 | A1* | 10/2016 | Hood ................... G08B 3/1016 |
| 2017/0315583 | A1* | 11/2017 | Ivanovic ............... H04B 1/385 |
| 2018/0295186 | A1* | 10/2018 | Schlapfer ............... H04L 67/02 |
| 2018/0325469 | A1 | 11/2018 | Fountaine |
| 2019/0108908 | A1* | 4/2019 | Faulks ................. G08B 27/005 |
| 2019/0327161 | A1 | 10/2019 | Cannell et al. |
| 2020/0319894 | A1 | 10/2020 | Golov |
| 2020/0329358 | A1 | 10/2020 | Hamre et al. |
| 2020/0335209 | A1 | 10/2020 | Holscher et al. |
| 2021/0045677 | A1 | 2/2021 | Ribble et al. |
| 2021/0081517 | A1 | 3/2021 | Atkinson et al. |
| 2021/0274034 | A1 | 9/2021 | Mase et al. |
| 2021/0319894 | A1 | 10/2021 | Sobol et al. |
| 2021/0350823 | A1 | 11/2021 | Wexler et al. |
| 2021/0375449 | A1* | 12/2021 | Christie ................. G16H 40/67 |
| 2022/0044772 | A1 | 2/2022 | Moghadam et al. |
| 2022/0101847 | A1* | 3/2022 | Receveur ............... G10L 15/22 |
| 2022/0180341 | A1 | 6/2022 | Sanidas et al. |
| 2022/0369983 | A1 | 11/2022 | Parale et al. |
| 2023/0195866 | A1 | 6/2023 | Hudgins et al. |
| 2024/0048657 | A1 | 2/2024 | Martin |
| 2024/0163604 | A1 | 5/2024 | Ayers |

FOREIGN PATENT DOCUMENTS

| | | |
|---|---|---|
| KR | 20140092396 A | 7/2014 |
| TW | I622024 B | 4/2018 |

OTHER PUBLICATIONS

Vocera Badge User Guide B3000n Compatible; Vocera Communications, Inc.; 2002-2016, last modified Jun. 28, 2016 (133 pages).

Vocera B-Series Badge User Guide; Vocera Communications, Inc.; 2002-2022, last modified Feb. 16, 2022 (123 pages).

Vocera User Guide Version 3.1; Vocera® Communications, Inc.; 2002-2005 (196 pages).

* cited by examiner

Place & receive calls or broadcasts
Users | Roles | Teams

Receive and respond to alerts

Use assignments

VOICE COMMUNICATION DEVICE HAVING LOCATING AND PAIRING AND OTHER IMPROVED BADGE FUNCTIONALITY

The present application claims the benefit, under 35 U.S.C. § 119(e), of U.S. Provisional Patent Application Nos. 63/764,945, filed Feb. 28, 2025, and 63/565,642, filed Mar. 15, 2024, each of which is hereby incorporated by reference herein in its entirety.

BACKGROUND

The present disclosure relates to wireless communication devices worn by caregivers in healthcare facilities and particularly, to wireless communication devices configured for voice-activated communication. More particularly, the present disclosure also relates to wireless devices that send signals to locating systems in healthcare facilities.

In the healthcare setting, caregivers are known to wear separate devices for voice communications and for locating and tracking the whereabouts of the caregivers. Such devices are sometimes interchangeably referred to as "badges" or "tags." The badges are oftentimes clipped onto the caregivers' clothing or are worn as a pendant of a necklace. One known voice communication device of this type is the VOCERA® badge available from Stryker Corporation of Kalamazoo, Michigan. One known locating and tracking system having locating tags is the HILLROM™ Precision Locating (HPL) System available from Hill-Rom Company, Inc. of Batesville, Indiana. In addition to voice communication badges and locating and tracking tags, caregivers also may wear other types of tokens such as access cards, identification (ID) tags, swipe cards, etc. Wearing multiple types of badges, tags, and tokens creates clutter and excess weight that is borne by caregivers. Thus, devices that lessen such clutter and weight would be welcome by caregivers.

Caregivers are also known to carry mobile phones having software that interfaces with a nurse call system and/or an electronic medical records system. Accordingly, nurse calls and medical device alerts are oftentimes communicated to both the voice communication badges and mobile phones of caregivers for display on respective display screens of such devices. As a result, each of the voice communication badges and mobile phones of caregivers may list duplicate nurse call and device alert messages for the caregivers to accept, reject, or transfer to other caregivers. Thus, inputs from the caregivers on two different devices may be required in some systems. Coordination between voice communication badges and mobile phones with regard to the handling of incoming nurse call and alert messages would also be welcome by caregivers.

SUMMARY

An apparatus, system, or method may comprise one or more of the features recited in the appended claims and/or the following features which, alone or in any combination, may comprise patentable subject matter:

According to a first aspect of the present disclosure, a healthcare communication system may be provided for use in a healthcare facility that may have a network that may include wireless access points (WAP's). The healthcare communication system of the first aspect may include a real-time locating system (RTLS) that may include a locating computer and a plurality of locating receivers that may be mounted within the healthcare facility. The locating receivers may be communicatively coupled to the locating computer. The healthcare communication system also may include a voice communication badge that may be configured to be worn by a caregiver and that may include a display, a microphone that may be configured to detect the caregiver's spoken commands, a plurality of buttons that may be spaced apart from the display and that may be used by the caregiver to select or alter first information appearing on the display, and circuitry that may include a wireless fidelity (WiFi) module that may be configured to (i) send and receive long range wireless signals to and from, respectively, one or more of the WAP's, and (ii) send and receive short range wireless signals. The circuitry also may include a location module that may be configured to emit beacon signals that may be received by at least one of the receivers of the RTLS. The locating computer may be configured to determine a location of the voice communication badge in the healthcare facility based on the beacon signals. The healthcare communication system of the first aspect may further include a software application that may be installed on a mobile phone of the caregiver. The software application may include instructions that, when executed by a processor of the mobile phone, may configure the mobile phone for short range wireless pairing with the voice communication badge via short rand wireless communication with the WiFi module. Subsequent to the short range wireless pairing, (i) selection of at least one button of the plurality of buttons to select or alter the first information also may select or alter second information appearing on a touchscreen of the mobile phone, and (ii) selection of an input field shown on the touchscreen of the mobile phone may select or alter the first information appearing on the display of the voice communication badge.

In some embodiments, the WiFi module of the first aspect may include a first antenna through which the long range wireless signals and the short range wireless signals may be sent and received. Optionally, the location module of the second aspect may include a second antenna through which the beacon signals are emitted. Further optionally, the beacon signals emitted by the location module of the first aspect may comprise ultra wideband (UWB) signals.

If desired, the locating computer of the first aspect may use a time difference of arrival (TDoA) methodology to determine the location of the voice communication badge based on arrival times of each of the beacon signals at multiple locating receivers of the plurality of locating receivers. In such embodiments, the beacon signals emitted by the location module of the second aspect may comprise ultra wideband (UWB) signals.

The present disclosure contemplates that the voice communication badge of the first aspect may include a housing, the display may be visible on a front wall of the housing, and the plurality of buttons may include a first set of buttons that may be accessible on a side wall of the housing. Optionally, the plurality of buttons of the first aspect may include a push-to-talk button that may be accessible on the front wall of the housing. Further optionally, the push-to-talk button of the first aspect may have an exposed first surface area that may be about the same size as an exposed second surface area of the display. The voice communication badge of the first aspect further may include a speaker that may be configured to provide audio outputs. Still further optionally, the display of the first aspect may be situated on the front wall between the push-to-talk button and the speaker.

In some embodiments of the healthcare communication system of the first aspect, the housing of the voice communication badge may be about 80 millimeters (mm) in height, 40 mm in width, and 19 mm in depth. Alternatively or additionally, the housing of the voice communication badge of the first aspect may occupy a volume no greater than about 60,800 mm$^3$.

If desired, the circuitry of the voice communication badge of the first aspect further may include a main control unit (MCU) integrated circuit (IC) chip that may be electrically coupled to the display, the microphone, the plurality of buttons, the WiFi module, and the location module. Also if desired, the WiFi module of the first aspect may be electrically coupled to the MCU IC chip via a first serial universal asynchronous receiver/transmitter (UART) connection and the location module of the first aspect may be electrically coupled to the MCU IC chip via a second serial UART connection.

The present disclosure contemplates that the WiFi module of the first aspect may be configured to establish short range wireless communications with one or more medical devices that may be located in a room in which the caregiver may be located. In such embodiments, the locating computer of the RTLS of the first aspect may be configured to determine that the one or more medical devices may be located in the room based on device information that may be transmitted from the voice communication badge. For example, the device information may be transmitted by the WiFi module of the voice communication badge of the first aspect to the one or more WAP's. Alternatively or additionally, the device information may be transmitted by the location module of the voice communication badge of the first aspect to one or more of the receivers of the plurality of receivers of the RTLS. Optionally, the one or more medical devices of the first aspect may include one or more of the following: a patient bed, a patient lift, an infusion pump, a sequential compression device (SCD), a physiological monitor, a dialysis machine, or a therapy device.

In some embodiments of the healthcare communication system of the first aspect, the locating computer may be configured to send caregiver proximity information for receipt by both the voice communication badge and the mobile phone of the caregiver to be shown on the display of the voice communication badge and on the touchscreen of the mobile phone. For example, the proximity information may identify any other caregivers that may be within a threshold distance from the caregiver. If desired, spoken commands received by the microphone from the caregiver may be transmitted as command signals via the WiFi module of the first aspect for receipt by a voice processing server that may be hosted by a third party provider.

If desired, the circuitry of the voice communication badge of the first aspect may be configured to send a broadcast message to a plurality of endpoint devices of a broadcast message group of recipients in response to a broadcast voice command received by the microphone or in response to use of one or more of the plurality of buttons to navigate to a broadcast transmission option on a menu appearing on the display. For example, the broadcast message may be a pre-recorded voice message or a pre-established text message, or may be a voice message spoken in real time by the caregiver. The broadcast message group by be configurable by use of the mobile phone or by use of a remote computer. Optionally, the broadcast message group may be stored in a directory of a server along with other broadcast message groups.

In some embodiments of the healthcare communication system of the first aspect, at least some of the plurality of endpoints to which the broadcast message may be sent may include other voice communication badges of the broadcast message group. Alternatively or additionally, at least some of the plurality of endpoints to which the broadcast message may be sent may include other mobile phones of the broadcast message group. Further alternatively or additionally, at least some of the plurality of endpoints to which the broadcast message may be sent may include hardwired phones. Still further alternatively or additionally, at least some of the endpoints to which the broadcast message may be sent may include communication devices of a nurse call system. Such communication devices of the nurse call system may include, for example, any one or more of the following: a master nurse station console, a graphical room station (GRS), a graphical staff station (GSS), a pillow speaker unit, and a patient bed.

Optionally, the circuitry of the voice communication badge of the first aspect may be configured to send a control message to a medical device to control a function of the medical device in response to a device voice command received by the microphone or in response to use of one or more of the plurality of buttons to navigate to a device control option on a menu appearing on the display. For example, the medical device may include a patient bed and the control message may result in a falls risk protocol of the patient bed being turned on or turned off. In such embodiments, the falls risk protocol, when turned on, may monitor bed status to assure that one or more siderails of the patient bed may be in respective raised positions, an upper frame of the patient bed may be in a lowered position relative to a base frame of the patient bed, and that a bed exit/patient position monitoring (PPM) system of the patient bed may be enabled to determine a position of a patient on the patient bed.

The present disclosure also contemplates that the control command may result in a vital signs monitoring function of the patient bed being turned on or turned off. If desired, the vital signs monitoring function may include detecting a heart rate and/or respiration rate of a patient that may be supported on the patient bed. Optionally, the control command may pertain to one or more of the following bed functions: raising, lowering, and/or tilting an upper frame of the patient bed relative to a base frame; raising or lowering an articulating mattress support deck section of the patient bed, and electrical braking or releasing of casters of the patient bed.

In some embodiments of the first aspect, the patient bed may include a mattress that may have one or more air bladders and a pneumatic system for inflating and deflating the one or more air bladders. In such embodiments, the control command may pertain to one or more of the following functions or therapies of the mattress accomplished by inflating and/or deflating the one or more air bladders: a turn assist function, a continuous lateral rotation therapy (CLRT), an alternating pressure (AP) therapy, a microclimate management (MCM) therapy, a percussion and vibration (P&V) therapy, and a heel relief function. Thus, the medical device of the first aspect may include a patient bed and, in such embodiments, the control command may be able to control any function from among a plurality of functions of the patient bed when the voice communication badge is located in a patient room with patient bed. However, if the voice communication badge is located outside of the patient room in which the patient bed is located, the control command only may be able to control a limited set of bed functions from among the plurality of bed functions.

If desired, at least one button of the plurality of buttons may be operable as a duress button which, in response to being pressed, may cause the circuitry of the voice communication badge to speed dial and/or send a duress message via the WiFi module to one or more programmed recipients.

Alternatively or additionally, receipt of a spoken duress command by the microphone of the voice communication badge may cause the circuitry to speed dial and/or send the duress message via the WiFi module to the one or more programmed recipients. Optionally, the voice communication badge may be configured for simultaneous login with a communication and alert handling application of the mobile phone.

In some embodiments of the healthcare communication system of the first aspect, the voice communication badge may be configured to receive a nurse call from a nurse call system having a plurality of devices from which the nurse call may originate. In such embodiments, the voice communication badge may be configured to permit a user to answer the nurse call by forming a voice communication link with a device of the plurality of devices from which the nurse call originated.

The present disclosure contemplates that the voice communication badge of the first aspect also may be communicatively couplable with the software application installed on the mobile phone via network infrastructure of a healthcare facility. Alternatively or additionally, the voice communication badge also may be communicatively couplable with the software application installed on the mobile phone via a cloud-based voice assistant server that may have a large language model (LLM) with retrieval augmented generation (RAG). Optionally, the short range wireless pairing between the mobile phone and the voice communication badge may include a Bluetooth Low Energy (BLE) communication link.

According to a second aspect of the present disclosure, a healthcare communication system may include a real-time locating system (RTLS) that, in turn, may include a locating computer and a plurality of locating receivers that may be mounted throughout a healthcare facility. The locating receivers may be communicatively coupled to the locating computer. The healthcare communication system of the second aspect also may include a voice communication badge that may include a housing that may be configured to be worn by a caregiver, a controller that may be carried by the housing, a display that may be coupled to the controller and that may be visible on a front wall of the housing, a microphone that may be coupled to the controller and configured to detect the caregiver's spoken commands, and a plurality of user inputs that may be carried by the housing and that may be spaced apart from the display. At least one user input of the plurality of user inputs may be used by the caregiver to select or alter first information appearing on the display. The voice communication badge of the second aspect may further include a speaker that may be coupled to the controller and that may be configured to provide audio outputs, a wireless fidelity (WiFi) module that may be carried by the housing and that may be coupled to the controller, and a location module that may be coupled to the controller and configured to emit beacon signals that are received by at least one of the receivers of the RTLS. The WiFi module of the second aspect may be configured to send and receive both WiFi signals and Bluetooth signals. The locating computer of the second aspect may be configured to determine a location of the voice communication badge in the healthcare facility based on the beacon signals. The healthcare communication system of the second aspect further may include a software application that may be installed on a mobile phone of the caregiver. The software application of the second aspect may include instructions that, when executed by a processor of the mobile phone, may configure the mobile phone for Bluetooth pairing with the voice communication badge. Subsequent to Bluetooth pairing, (i) selection of the at least one user input of the voice communication badge of the second aspect also may select or alter second information appearing on a touchscreen of the mobile phone, and (ii) selection of an input field shown on the touchscreen of the mobile phone may select or alter the first information appearing on the display of the voice communication badge of the second aspect.

In some embodiments, the WiFi module of the second aspect may include a first antenna through which the WiFi signals and the Bluetooth signals may be sent and received. Optionally, the location module of the second aspect may include a second antenna through which the beacon signals are emitted. Further optionally, the beacon signals emitted by the location module of the second aspect may comprise ultra wideband (UWB) signals.

If desired, the locating computer of the second aspect may use a time difference of arrival (TDoA) methodology to determine the location of the voice communication badge based on arrival times of each of the beacon signals at multiple locating receivers of the plurality of locating receivers. In such embodiments, the beacon signals emitted by the location module of the second aspect may comprise ultra wideband (UWB) signals.

The present disclosure contemplates that the voice communication badge of the second aspect may include a housing, the display may be visible on a front wall of the housing, and the plurality of user inputs may include a first set of buttons that may be accessible on a side wall of the housing. Optionally, the plurality of user inputs of the second aspect may include a push-to-talk button that may be accessible on the front wall of the housing. Further optionally, the push-to-talk button of the second aspect may have an exposed first surface area that may be about the same size as an exposed second surface area of the display. Still further optionally, the display of the second aspect may be situated on the front wall between the push-to-talk button and the speaker.

In some embodiments of the healthcare communication system of the second aspect, the housing of the voice communication badge may be about 80 millimeters (mm) in height, 40 mm in width, and 19 mm in depth. Alternatively or additionally, the housing of the voice communication badge of the second aspect may occupy a volume no greater than about 60,800 $mm^3$.

If desired, the circuitry of the voice communication badge of the second aspect further may include a main control unit (MCU) integrated circuit (IC) chip that may be electrically coupled to the display, the microphone, the plurality of user inputs, the WiFi module, and the location module. Also if desired, the WiFi module of the second aspect may be electrically coupled to the MCU IC chip via a first serial universal asynchronous receiver/transmitter (UART) connection and the location module of the second aspect may be electrically coupled to the MCU IC chip via a second serial UART connection.

The present disclosure contemplates that the WiFi module of the second aspect may be configured to establish Bluetooth communications with one or more medical devices that may be located in a room in which the caregiver may be located. In such embodiments, the locating computer of the RTLS of the second aspect may be configured to determine that the one or more medical devices are located in the room based on device information that may be transmitted from the voice communication badge. For example, the device information may be transmitted by the WiFi module of the voice communication badge of the second aspect. Alternatively or additionally, the device information may be transmitted by the location module of the voice communication badge of the second aspect to one or more of the receivers of the plurality of receivers of the RTLS. Optionally, the one or more medical devices of the second aspect may include one or more of the following: a patient bed, a patient lift, an infusion pump, a sequential compression device (SCD), a physiological monitor, a dialysis machine, or a therapy device.

In some embodiments of the healthcare communication system of the second aspect, the locating computer may be configured to send caregiver proximity information for receipt by both the voice communication badge and the mobile phone of the caregiver to be shown on the display of the voice communication badge and on the touchscreen of the mobile phone. For example, the proximity information may identify any other caregivers that may be within a threshold distance from the caregiver. If desired, spoken commands received by the microphone from the caregiver may be transmitted as command signals via the WiFi module of the second aspect for receipt by a voice processing server that may be hosted by a third party provider.

With regard to the healthcare communication system of the first and second aspects, the first information and the second information both may include a list of alert messages that may originate from one or more patients that may be assigned to the caregiver or from one or more medical devices that may be located in one or more patient rooms that may be assigned to the caregiver. For example, the one or more medical devices of the first and second aspects may include one or more of the following: a patient bed, a patient lift, an infusion pump, a sequential compression device (SCD), a physiological monitor, a dialysis machine, or a therapy device.

Optionally, the plurality of user inputs of the voice communication badge of the second aspect may include a microphone that may be coupled to the controller for receipt of voice commands, Further optionally, the plurality of user inputs of the voice communication badge of the second aspect may include a plurality of buttons that may be carried by the housing and that may be coupled to the controller. If desired, the controller and the WiFi module of the voice communication badge of the second aspect may cooperate to send a broadcast message to a plurality of endpoint devices of a broadcast message group of recipients in response to a broadcast voice command received by the microphone or in response to use of one or more of the plurality of buttons to navigate to a broadcast transmission option on a menu appearing on the display. For example, the broadcast message of the second aspect may include a pre-recorded voice message or a pre-established text message, or may be a voice message spoken in real time by the caregiver. The broadcast message group of the second aspect may bye configurable by use of the mobile phone or by use of a remote computer. Optionally, the broadcast message group of the second aspect may be stored in a directory of a server along with other broadcast message groups.

In some embodiments of the healthcare communication system of the second aspect, at least some of the plurality of endpoints to which the broadcast message may be sent may include other voice communication badges of the broadcast message group. Alternatively of additionally, at least some of the plurality of endpoints to which the broadcast message may be sent may include other mobile phones of the broadcast message group. Further alternatively or additionally, at least some of the plurality of endpoints to which the broadcast message may be sent may include hardwired phones. Still further alternatively or additionally, at least some of the endpoints to which the broadcast message may be sent may include communication devices of a nurse call system. Such communication devices of the nurse call system of the second aspect may include any one or more of the following: a master nurse station console, a graphical room station (GRS), a graphical staff station (GSS), a pillow speaker unit, and a patient bed.

With regard to the voice communication badge of the second aspect in which the at least one user input includes a microphone coupled to the controller for receipt of voice commands and a plurality of buttons carried by the housing and coupled to the controller, the controller and the wireless module may cooperate to send a control message to a medical device to control a function of the medical device in response to a device voice command received by the microphone or in response to use of one or more of the plurality of buttons to navigate to a device control option on a menu appearing on the display. For example, the medical device may include a patient bed and the control message may result in a falls risk protocol of the patient bed being turned on or turned off. In such embodiments of the second aspect, the falls risk protocol, when turned on, may monitor bed status to assure that one or more siderails of the patient bed may be in respective raised positions, an upper frame of the patient bed may be in a lowered position relative to a base frame of the patient bed, and that a bed exit/patient position monitoring (PPM) system of the patient bed may be enabled to determine a position of a patient on the patient bed.

The present disclosure also contemplates that the control command may result in a vital signs monitoring function of the patient bed of the second aspect being turned on or turned off. If desired, the vital signs monitoring function may include detecting a heart rate and/or respiration rate of a patient that may be supported on the patient bed. Optionally, the control command of the second aspect may pertain to one or more of the following bed functions: raising, lowering, and/or tilting an upper frame of the patient bed relative to a base frame; raising or lowering an articulating mattress support deck section of the patient bed, and electrical braking or releasing of casters of the patient bed.

In some embodiments of the second aspect, the patient bed may include a mattress that may have one or more air bladders and a pneumatic system for inflating and deflating the one or more air bladders. In such embodiments, the control command may pertain to one or more of the following functions or therapies of the mattress accomplished by inflating and/or deflating the one or more air bladders: a turn assist function, a continuous lateral rotation therapy (CLRT), an alternating pressure (AP) therapy, a microclimate management (MCM) therapy, a percussion and vibration (P&V) therapy, and a heel relief function. Thus, the medical device of the second aspect may include a patient bed and, in such embodiments, the control command may be able to control any function from among a plurality of functions of the patient bed when the voice communication badge is located in a patient room with patient bed. However, if the voice communication badge of the second aspect is located outside of the patient room in which the patient bed is located, the control command only may be able to control a limited set of bed functions from among the plurality of bed functions.

As noted previously, the plurality of user inputs of the voice communication badge of the second aspect may include a plurality of buttons that may be carried by the housing and that may be coupled to the controller. In such embodiments, at least one button of the plurality of buttons may be operable as a duress button which, in response to being pressed, may cause the controller to speed dial and/or send a duress message via the WiFi module to one or more programmed recipients. Alternatively or additionally, the at least one user input of the voice communication badge of the second aspect may include a microphone that may be coupled to the controller for receipt of voice commands, and receipt of a spoken duress command by the microphone may cause the controller to speed dial and/or send the duress message via the wireless module to the one or more programmed recipients. Optionally, the voice communication badge of the second aspect may be configured for simultaneous login with a communication and alert handling application of the mobile phone.

In some embodiments of the healthcare communication system of the second aspect, the voice communication badge may be configured to receive a nurse call from a nurse call system having a plurality of devices from which the nurse call may originate. In such embodiments, the voice communication badge of the second aspect may be configured to permit a user to answer the nurse call by forming a voice communication link with a device of the plurality of devices from which the nurse call originated.

The present disclosure contemplates that the voice communication badge of the second aspect also may be communicatively coupleable with the software application installed on the mobile phone via network infrastructure of a healthcare facility. Alternatively or additionally, the voice communication badge of the second aspect also may be communicatively coupleable with the software application installed on the mobile phone via a cloud-based voice assistant server that may have a large language model (LLM) with retrieval augmented generation (RAG). Optionally, the Bluetooth pairing between the mobile phone and the voice communication badge of the second aspect may include a Bluetooth Low Energy (BLE) communication link.

According to a third aspect of the present disclosure, a healthcare communicator may include a voice communication badge which may, in turn, include a housing that may be configured to be worn by a caregiver, a controller that may be carried by the housing, a display that may be coupled to the controller and that may be visible on the housing, a microphone that may be coupled to the controller and that may be configured to detect the caregiver's spoken commands, and at least one user input that may be carried by the housing. The at least one user input may be usable by the caregiver to select or alter first information that may appear on the display. The voice communication badge of the third aspect may also include a speaker that may be coupled to the controller and that may be configured to provide audio outputs and a wireless module that may be carried by the housing and that may be coupled to the controller. The wireless module may be configured to send and receive at least one of long range signals and short range signals. The voice communication badge of the third aspect further may include a location module that may be coupled to the controller and that may be configured to emit or receive beacon signals that may be communicated with a real-time locating system (RTLS) that may have a locating computer that may be configured to determine a location of the voice communication badge in the healthcare facility based on the beacon signals, and a pairing module that may be communicatively coupled with a software application that may be installed on a mobile phone of the caregiver. Selection of an input of the mobile phone may select or alter the first information that may appear on the display of the voice communication badge.

In some embodiments of the voice communication badge of the healthcare communicator of the third aspect, the wireless module and the pairing module may be integrated together into a common module. Optionally, the healthcare communicator of the third aspect may be provided in combination with any of one or more of the features of the first aspect and/or in combination with any one or more of the features of the second aspect. Further optionally, selection of the at least one user input of the communication badge may select or alter second information that may appear on the mobile phone.

Optionally, the at least one user input of the voice communication badge of the third aspect may include a plurality of buttons that may be carried by the housing and that may be coupled to the controller. If desired, the controller and the wireless module of the voice communication badge of the third aspect may cooperate to send a broadcast message to a plurality of endpoint devices of a broadcast message group of recipients in response to a broadcast voice command that may be received by the microphone or in response to use of one or more of the plurality of buttons to navigate to a broadcast transmission option on a menu that may appear on the display. For example, the broadcast message of the third aspect may include a pre-recorded voice message or a pre-established text message, or may be a voice message spoken in real time by a user. The broadcast message group of the third aspect may be configurable by use of the mobile phone or by use of a remote computer. Optionally, the broadcast message group may be stored in a directory of a server along with other broadcast message groups.

In some embodiments of the healthcare communicator of the third aspect, at least some of the plurality of endpoints to which the broadcast message may be sent may comprise other healthcare communicators of the broadcast message group. Alternatively of additionally, at least some of the plurality of endpoints to which the broadcast message may be sent may include other mobile phones of the broadcast message group. Further alternatively or additionally, at least some of the plurality of endpoints to which the broadcast message may be sent may include hardwired phones. Still further alternatively or additionally, at least some of the endpoints to which the broadcast message may be sent may include communication devices of a nurse call system. Such communication devices of the nurse call system of the third aspect may include any one or more of the following: a master nurse station console, a graphical room station (GRS), a graphical staff station (GSS), a pillow speaker unit, and a patient bed.

With regard to the healthcare communicator of the third aspect in which the at least one user input includes a plurality of buttons carried by the housing and coupled to the controller, the controller and the wireless module may cooperate to send a control message to a medical device to control a function of the medical device in response to a device voice command received by the microphone or in response to use of one or more of the plurality of buttons to navigate to a device control option on a menu that may appear on the display. For example, the medical device may include a patient bed and the control message may result in a falls risk protocol of the patient bed being turned on or turned off. In such embodiments of the third aspect, the falls risk protocol, when turned on, may monitor bed status to assure that one or more siderails of the patient bed may be in respective raised positions, an upper frame of the patient bed may be in a lowered position relative to a base frame of the patient bed, and that a bed exit/patient position monitoring (PPM) system of the patient bed may be enabled to determine a position of a patient on the patient bed.

The present disclosure also contemplates that the control command may result in a vital signs monitoring function of the patient bed of the third aspect being turned on or turned off. If desired, the vital signs monitoring function may include detecting a heart rate and/or respiration rate of a patient supported on the patient bed. Optionally, the control command of the third aspect may pertain to one or more of the following bed functions: raising, lowering, and/or tilting an upper frame of the patient bed relative to a base frame; raising or lowering an articulating mattress support deck section of the patient bed, and electrical braking or releasing of casters of the patient bed.

In some embodiments of the third aspect, the patient bed may include a mattress that may have one or more air bladders and a pneumatic system for inflating and deflating the one or more air bladders. In such embodiments, the control command may pertain to one or more of the following functions or therapies of the mattress accomplished by inflating and/or deflating the one or more air bladders: a turn assist function, a continuous lateral rotation therapy (CLRT), an alternating pressure (AP) therapy, a microclimate management (MCM) therapy, a percussion and vibration (P&V) therapy, and a heel relief function. Thus, the medical device of the third aspect may include a patient bed and, in such embodiments, the control command may be able to control any function from among a plurality of functions of the patient bed when the healthcare communicator is located in a patient room with patient bed. However, if the healthcare communicator of the third aspect is located outside of the patient room in which the patient bed is located, the control command only may be able to control a limited set of bed functions from among the plurality of bed functions.

As noted previously, the at least one user input of the voice communication badge of the third aspect may include a plurality of buttons that may be carried by the housing and that may be coupled to the controller. In such embodiments, at least one button of the plurality of buttons may be operable as a duress button which, in response to being pressed, may cause the controller to speed dial and/or send a duress message via the wireless module to one or more programmed recipients. Alternatively or additionally, receipt of a spoken duress command by the microphone may cause the controller to speed dial and/or send the duress message via the wireless module to the one or more programmed recipients. Optionally, the healthcare communicator of the third aspect may be configured for simultaneous login with a communication and alert handling application of the mobile phone.

In some embodiments of the healthcare communicator of the third aspect, the healthcare communicator may be configured to receive a nurse call from a nurse call system having a plurality of devices from which the nurse call may originate. In such embodiments, the healthcare communicator of the third aspect may be configured to permit a user to answer the nurse call by forming a voice communication link with a device of the plurality of devices from which the nurse call originated.

The present disclosure contemplates that the pairing module of the voice communication badge of the third aspect may be communicatively coupled with the software application installed on the mobile phone via network infrastructure of a healthcare facility. Alternatively or additionally, the pairing module of the voice communication badge of the third aspect may be communicatively coupled with the software application installed on the mobile phone via a cloud-based voice assistant server that may have a large language model (LLM) with retrieval augmented generation (RAG). Optionally, the pairing module of the voice communication badge of the third aspect may be communicatively coupled with the software application installed on the mobile phone via a Bluetooth Low Energy (BLE) communication link.

According to a fourth aspect of the present disclosure, a healthcare communication method for a healthcare facility may include providing a voice communication badge to a caregiver. The voice communication badge may include a housing, a controller that may be carried by the housing, a display that may be coupled to the controller and that may be visible to the caregiver, a microphone that may be coupled to the controller and that may be configured to detect the caregiver's spoken commands, a plurality of user inputs that may be carried by the housing, a speaker that may be coupled to the controller and that may be configured to provide audio outputs, a wireless communication module may be carried by the housing and that may be coupled to the controller, and a location module that may be coupled to the controller. The method may further include sending and receiving, with the wireless communication module of the voice communication badge, long range wireless signals and short range wireless signals; emitting, with a location module of the voice communication badge, beacon signals that may be received by at least one receiver of a real-time locating system (RTLS); determining, with a locating computer, a location of the voice communication badge in the healthcare facility based on the beacon signals; associating a mobile phone of the caregiver with the voice communication badge; and using, after the voice communication badge and the mobile phone are associated, the at least one user input to select or alter first information appearing on the display of the voice communication badge which may result in also selecting or altering, respectively, second information that may appear on the mobile phone, and/or using, after the voice communication badge and the mobile phone are associated, an input field shown on the mobile phone which may result in selecting or altering third information that may appear on the display of the voice communication badge.

According to a fifth aspect of the present disclosure, one or more tangible computer-readable storage media may include a plurality of instructions that, when executed, may cause a healthcare communication system to: send from a wireless communication module of a voice communication badge of a caregiver, long range wireless signals and short range wireless signals; emit from a location module of the circuitry of the voice communication badge, beacon signals that may be received by at least one receiver of a real-time locating system (RTLS); determine, with a locating computer, a location of the voice communication badge in the healthcare facility based on the beacon signals; associate a mobile phone of the caregiver with the voice communication badge; and after the voice communication badge and the mobile phone are associated, receive at least one user input on the voice communication badge to select or alter first information that may appear on a display of the voice communication badge which may result in also selecting or altering, respectively, second information appearing on the mobile phone, and/or, after the voice communication badge and the mobile phone are associated, receive a selection on an input field shown on the mobile phone which may result in selecting or altering third information that may appear on the display of the voice communication badge.

According to a sixth aspect, the present disclosure, therefore, contemplates a healthcare communication system that may include a real-time locating system (RTLS) and a voice communication badge that may include a housing, a controller, a display, a microphone for spoken commands, user inputs, a speaker, a wireless module that may send long range and short range signals, a location module that may emit beacon signals that may be received by the RTLS which may determine a location of the voice communication badge, and a software application that may pair the badge and a mobile phone. Selection of an input field that may be shown on a touchscreen of the mobile phone of the sixth aspect may select or alter first information that may appearing on the display of the voice communication badge.

According to a seventh aspect, the present disclosure also contemplates a healthcare communicator that may include a housing, a controller, a display, a microphone to detect spoken commands, a user input to select or alter first information on the display, a speaker, a wireless module that may be configured to send at least one of long range signals and short range signals, a location module that may be configured to emit or receive beacon signals that may be communicated with a real-time locating system (RTLS), and a pairing module that may be communicatively coupled with an application on a mobile phone of a caregiver. Selection of an input on a touchscreen of the mobile phone of the seventh aspect may select or alter the first information that may appear on the display of the badge.

A method of making any of the healthcare communication systems of any of the first, second, or sixth aspects is contemplated herein. A method of using any of the healthcare communication systems of any of the first, second, or sixth aspects is also contemplated herein. A method of making the healthcare communicator of the third aspect or the seventh aspect is contemplated herein. A method of using the healthcare communicator of the third aspect or the seventh aspect is also contemplated herein. Other methods, including the method of the fourth aspect, in combination with any of the methods of making or using the healthcare communication systems of any of the first, second, or sixth aspects, or the healthcare communicator of the third and seventh aspects are contemplated as well.

A tangible computer readable storage media including a plurality of instructions that, when executed, implement any one or more of the functions of the healthcare communication systems of any of the first, second or sixth aspects is contemplated herein. A tangible computer readable storage media including a plurality of instructions that, when executed, implement any one or more of the functions of the healthcare communicator of the third aspect or the seventh aspect is also contemplated herein. Other tangible computer readable storage media, including the one or more tangible computer readable storage media of the fifth aspect, in combination with any of the tangible computer readable storage media for implementing any of the functions of the healthcare communication systems of any of the first, second, or sixth aspects, or the healthcare communicator of the third and seventh aspects are contemplated as well.

Additional features, which alone or in combination with any other feature(s), such as those listed above, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures, in which.

DETAILED DESCRIPTION

Figures 1, 2, 3:
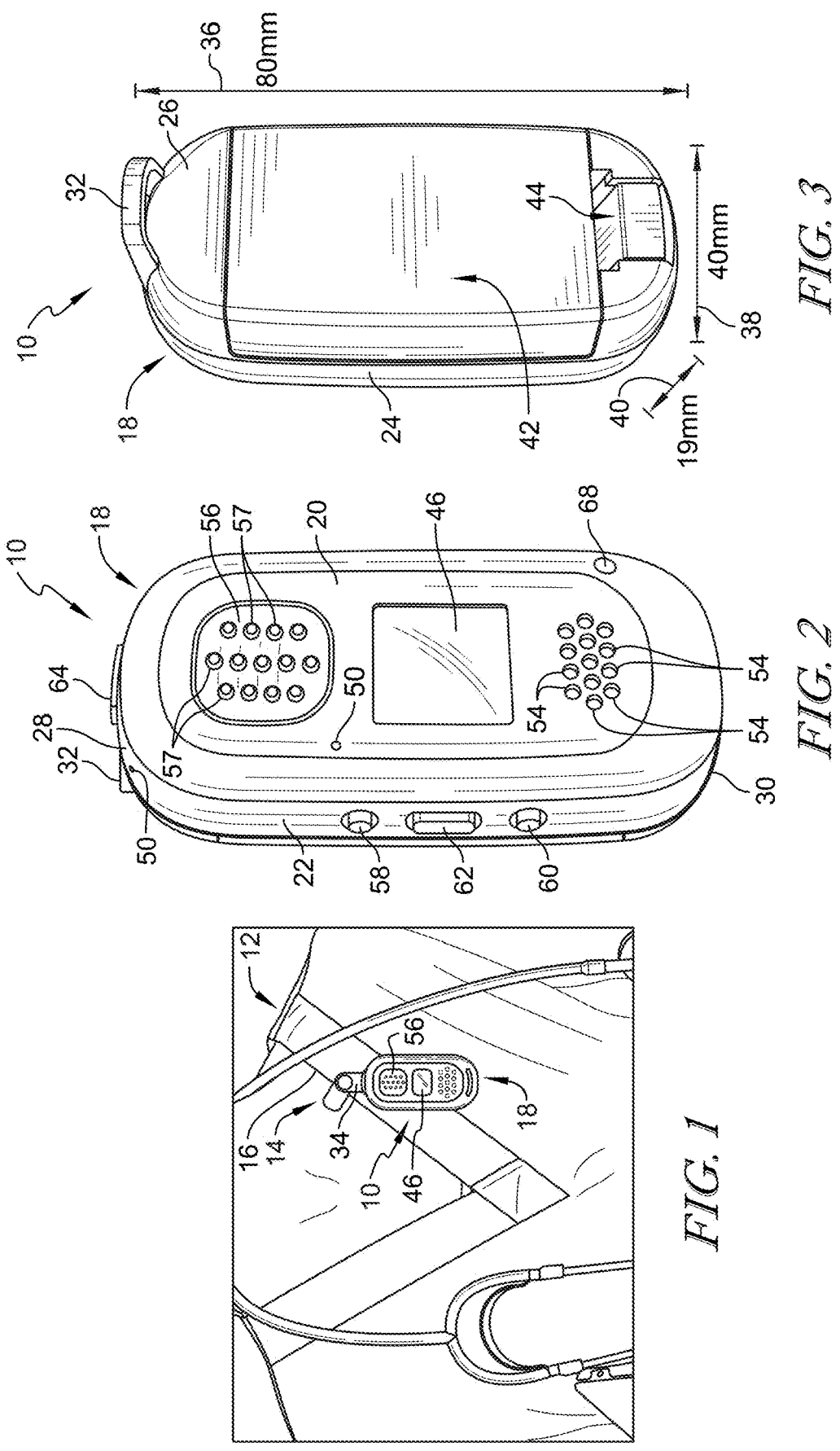
FIG. 1 is front elevation view of a voice communication badge clipped to a shirt of a caregiver.
FIG. 2 is a front perspective view of the voice communication badge of FIG. 1 showing a display visible on a front wall of a housing of the voice communication badge, a push-to-talk button above the display, a speaker grill beneath the display, and three buttons accessible on a side wall of the housing of the voice communication badge.
FIG. 3 is a rear perspective view of the voice communication badge of FIGS. 1 and 2 showing a removable battery cover of the housing forming a back portion of the housing and showing an integrally molded connection loop at a top region of the housing.

A voice communication badge 10 is configured for attachment to a garment 12 of a caregiver as shown in FIG. 1. In the illustrative example, badge 10 has a clip 14 that releasably grips a neck opening 16 of garment 12. In other instances, badge 10 is attached to a necklace (not shown) worn by the caregiver such that badge 10 is worn as a pendant of the necklace. Thus, the word "badge" is used broadly herein to connote a wearable, carriable, or otherwise portable communication device. Badge 10 includes a housing 18 having a front wall 20, a first side wall 22, a second side wall 24, a rear wall 26, a top wall 28, and a bottom wall 30 as shown in FIGS. 2 and 3. An attachment feature in the form of a connection loop 32 in the illustrative embodiment is molded integrally at the junction between the rear wall 26 and top wall 28 and extends rearwardly in generally perpendicular relation with rear wall 26. Loop 32 is configured to receive a lanyard, a clip, a band configured to be worn around a body part, such as a wrist or neck, etc. For example, a strap 34 extending from clip 14 is received through loop 32 to connect clip 14 to badge 10. When used as a necklace pendant, the necklace band extends through loop 32 in some such embodiments.

As is apparent in FIGS. 2 and 3, badge 10 is rounded at the junctions between all of walls 20, 22, 24, 26, 28, 30 of housing 18. In the illustrative embodiment, housing 18 of badge 10 has a height dimension 36 of about 80 millimeters (mm), a width dimension 38 of about 40 mm, and a depth dimension 40 of about 19 mm as shown in FIG. 3. Thus, width 38 is about half the length of height 36 and depth 40 is about half the length of width 38 in the illustrative embodiment. Because the corner regions between walls 20, 22, 24, 26, 28, 30 of housing 18 are rounded, housing 18 occupies no more than about 60,800 mm$^3$ (e.g., 80 mm×40 mm×19 mm=60,800 mm$^3$). Housing 18 is molded or otherwise made from a durable plastics material (e.g., polycarbonate or polypropylene) in the illustrative embodiment. For example, pieces of housing 18 are individually molded and then assembled together to provide the overall housing 18 of badge 10. In other embodiments, housing 18, or pieces thereof, are made from other materials of suitable strength such as metal materials including aluminum, stainless steel, and the like.

Housing 18 includes a removable battery cover 42, a main part of which serves as a portion of rear wall 26 and side parts of which serve as portions of respective side walls 22, 24 of housing 18. Battery cover 42 includes an integrally molded latch 44 which can be manually flexed by a user (e.g., caregiver) to permit removal of battery cover 42 from the remainder of housing 42. In some embodiments, removal of battery cover 42 permits access to a battery storage compartment (not shown) of badge 10 for removal and replacement of one or more batteries 43 (e.g., AA batteries, AAA batteries, a 9 Volt battery, or a custom-designed battery) (see FIG. 4) that power badge 10. In other embodiments, the battery that powers badge 10 is integrated into battery cover 42. In such embodiments, the integrated battery is removed from the battery compartment of housing 18 when battery cover 42 is detached from the main part of housing 18. In some embodiments, the battery integrated with battery cover 42 is of the type depicted in U.S. Design application Ser. No. 29/936,716, filed Apr. 10, 2024 and titled "Battery," which is hereby incorporated by reference herein. Batteries 43 used in badge 10 may be re-chargeable and/or replaceable, including batteries that are recharged inductively.

In some embodiments, battery 43 and/or battery 43 and cover 42 when battery 43 is integrated with cover 42, are hot swappable with a new battery and/or integrated cover 42 and battery 43. That is, when battery 43 (and cover 42 in integrated embodiments) are removed for replacement with a new battery 43, the user of badge 10 stays logged into badge 10 for a predetermined period of time. For example, the predetermined period of time for remaining logged into badge 10 is up to 2 hours, if desired, but can be programmed for a lesser amount of time such as about 10 seconds, 30 seconds, 2 minutes, etc., just to give some arbitrary examples. By having such hot swappable batteries 43 for badge 10, users are prevented from having to log into their respective badge 10, again, after an old battery 43 is swapped out for a new one.

Badge 10 further includes a display 46 disposed on housing 18 and visible on front wall 20 in a central region thereof as best shown in FIG. 2. In the illustrative embodiment, badge 10 includes three microphones 48, shown in FIG. 4, that are configured to detect the caregiver's spoken commands and that are aligned with respective mic openings 50 of housing 18. Two of openings 50 are visible in FIG. 2 with one being formed in front wall 20 above and to the left of display 46 and another being formed in the left rounded corner defined by the junction of top wall 28 and side wall 22. The third opening (not shown) is formed in the right rounded corner defined by the junction of top wall 28 and side wall 24. By providing three microphones 48 within badge 10 at different locations, commands spoken by the caregiver wearing badge 10 is detected even if the caregiver is wearing personal protective equipment (PPE) such as a mask. The use of three microphones 48 prevents accidental wake words, detected by only one of the microphones 48, for example, from waking badge 10 from a dormant state (aka sleep state).

Figure 4:
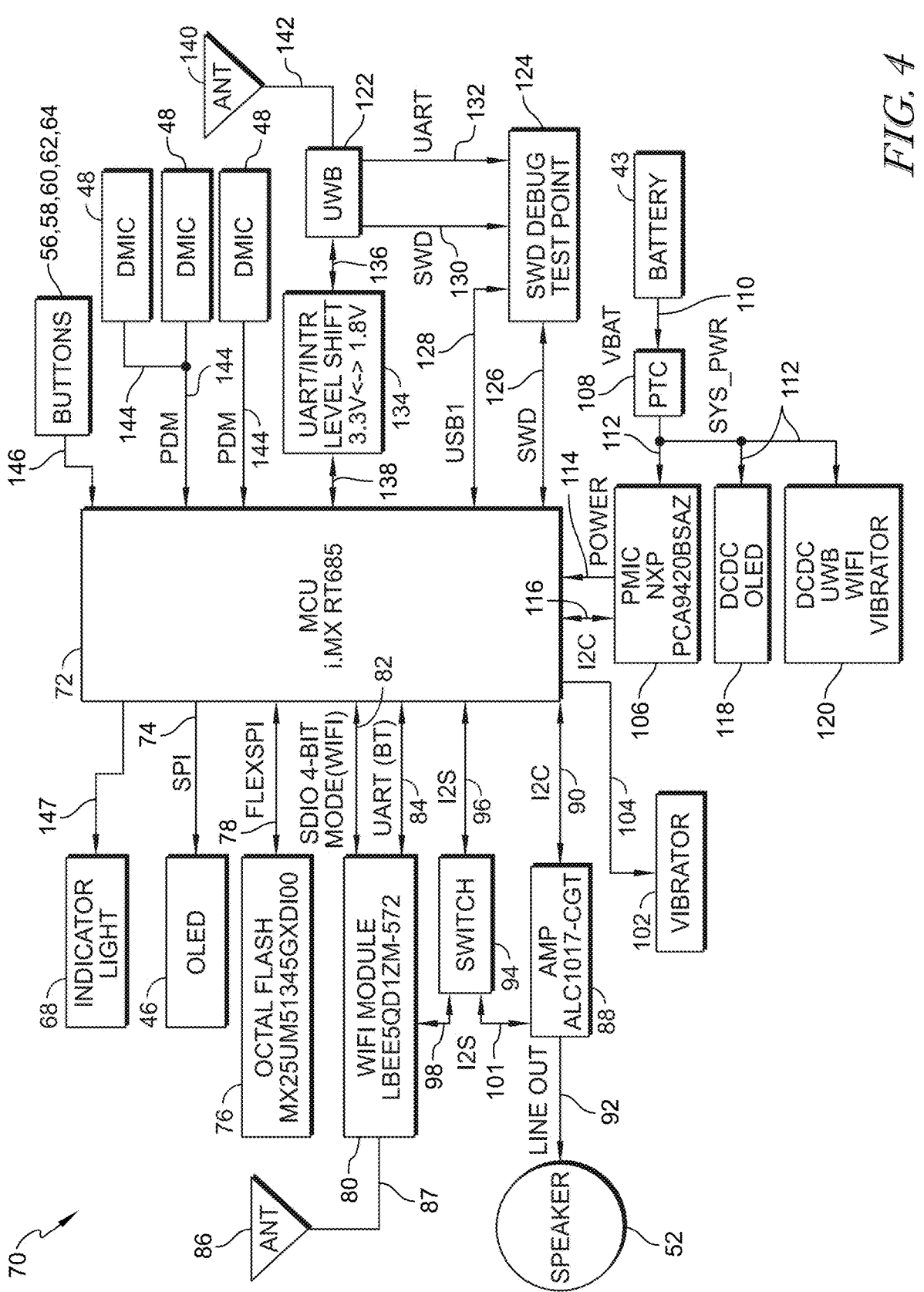
FIG. 4 is a block diagram showing various circuit components included in circuitry of the voice communication badge of FIGS. 1-4.

Badge 10 also includes a speaker 52, shown in FIG. 4, that provides audio outputs from badge 10. For example, speaker 52 is configured to convert an inaudible electromagnetic wave input into an audible sound wave output. Front wall 20 of housing 18 has a plurality of speaker openings 54 that are aligned with speaker 52. Holes 50, 54 are provided in housing 18 to lessen the attenuation of sound received by microphones 48 and output through speaker 52, respectively. Badge 10 further includes a voice command button 56 (aka a push-to-talk button 56) that is pressed by the caregiver to activate or turn on microphones 48 for a period of time, such as about 10 seconds, to receive the caregiver's spoken commands. It should be appreciated that microphone activation time periods of less than 10 seconds or greater than 10 seconds are within the scope of the present disclosure at the discretion of the badge designer or programmer. Illustrative button 56 includes a plurality of bumps or protrusions 57 to provide the caregiver with tactile feedback as to the location of button 56 on front wall 20 of badge 10.

In the illustrative embodiment of badge 10, the exposed surface area of push-to-talk button 56 is substantially equivalent to the exposed surface area of display 46. For example, button 56 and display 46 are each roughly square-shaped in the illustrative embodiment with dimensions of about 20 mm by about 20 mm resulting in exposed surface areas of about 400 mm$^2$ for each. Badges 10 having displays 46 and buttons 56 with dimensions greater than 20 mm by 20 mm, or less than 20 mm by 20 mm, are within the scope of the present disclosure, as are displays 46 and buttons 56 having other shapes such as rectangular, oval, circular, etc. Also in the illustrative embodiment, display 46 is situated between speaker 52 and button 56, with speaker 52 being situated at the bottom portion of housing 18 and button 56 being situated at the top portion of housing 18.

Display 46 of badge 10 is operated to display messages, notifications, alerts, tasks, call contact options, device settings, user preferences, and the like. These are generally shown in lists or menus on display 46. Providing display 46 on the front wall 20 of housing 18 allows the caregiver, or other user, to grasp the first and/or second side walls 22, 26 of badge 10 without interfering with or obscuring the visibility of display 46. In the illustrative example, display 46 is an organic light emitting diode (OLED) display which does not operate as a touchscreen but is operable to display images in a variety of colors (e.g., red, pink, purple, magenta, blue, green, yellow, etc.). In other embodiments, display 46 is configured as a user-interface, such as a touchscreen display.

For purposes of scrolling through items on the lists or menus displayed on illustrative display 46, badge 10 includes a scroll up button 58 to scroll up a list of the items appearing on display 46, a scroll down button 60 to scroll down the list of the items appearing on display 46, and a select button 62 to select a highlighted item appearing on display 46 as shown best in FIG. 2. In the illustrative example, buttons 58, 60, 62 protrude by a small amount (e.g., about 1-4 mm) from side wall 22 of housing 18 in a mid-region thereof so that the set of buttons 58, 60, 62 are generally horizontally aligned with display 46. The outer exposed surfaces of buttons 58, 60 are generally circular and the outer exposed surface of button 62 is generally oval such that button 62 is larger than buttons 58, 60 for ease of selection by the caregiver.

By using buttons 58, 60, 62, the caregiver in possession of badge 10 is able to select one of the selectable items, which in some instances, results in a subsequent and different view, or screen, appearing on display 46. In this way, the subsequent screen may be a second level screen relative to the previous screen (e.g., displayed after one user input). Such a hierarchy of screens appearing on display 46 helps in preventing inadvertent activation of a function of the badge 10. In this way, a plurality of second user options may be displayed on display 46 in response to a selection of one of a first plurality of first user options, and a third plurality of user options may be displayed on display 46 in response to selection of one of the plurality of the second user options. Further, buttons 58, 60 are usable to control a volume level of the sound output from speaker 52. In this regard, the caregiver first provides inputs using buttons 58, 60, 62 to navigate to a volume control screen. Furthermore, selection of voice command button 56 provides causes a corresponding screen to appear on display 46 in order to access various databases related to the care facility, including, but not limited to call contact databases, provider grouping databases, etc.

Notifications displayed on display 46, or emitted through the speaker 52, include messages (e.g. voice, sound, or text) originating from other devices of a network 100 (FIG. 5) such as other badges 10 or other communication devices such as mobile phones, graphical room stations (GRS's) of a nurse call system, master nurse call station handsets, wired telephone handsets, and the like, as well as alerts or nurse calls originating from medical devices such as hospital beds, infusion pumps, physiological monitors (e.g., heart rate monitors, respiration rate monitors, pulse oximeters, thermometers, and the like), pillow speaker units, and the like according to the present disclosure. The messages may include caller name information, call type information, countdown timer messages (for example, countdown timers from which have reached a minimum threshold), global messages generated for pre-determined groups of staff (for example, all caregivers having a specific certification), automated messages from caregiver monitoring systems, call response messages (for example, information request calls and/or equipment request calls), and direct caregiver messages (for example, messages received from other caregivers).

In addition to, or in lieu of buttons 58, 60, 22, badge 10 may include a variety of other selectable features such as soft key shown on screen 46, hard buttons and/or switches at other locations of housing 18, inputs having button-like tactile features (e.g., membrane switch buttons), and/or combinations thereof, etc. For example, badge 10 includes an additional button 64 at the top of housing 18. As shown in FIG. 2, button 64 projects slightly (e.g., about 1-4 mm) from top wall 28 of housing 18. Button 64 is configurable at the discretion of an administrator of system 100. That is, button 64 can be designated to have a specific meaning such as completion of rounds, request for housekeeping, or caregiver duress, just to name a few. For example, if button 64 is designated as a caregiver duress button, then button 64 is pressed by the caregiver to summon help from other caregivers or hospital staff in emergency situations, such as to deal with a combative or otherwise uncooperative patient, for example. In the illustrative example, duress button 64 is shaped similarly to button 62 so as to have an oval-shaped exposed outer surface.

In some embodiments, button 64 is configurable by associating one or more speed dial phone numbers therewith. Thus, if button 64 is used as a caregiver duress button, pressing button 64 results in the particular, pre-defined speed dial number(s) being called. The speed dial number(s) may correspond, for example, to the mobile phone numbers or to ID's of other badges 10 of one or more particular caregivers or staff members (e.g., a security officer, orderly, charge nurse, etc.) or other phone number(s) in the healthcare facility (e.g., a phone number of a phone at a master nurse station or a security office). A voice communication channel is then opened automatically between badge 10 and the communication device (e.g., wireless mobile phone, hardwired telephone, or badge) corresponding to the pre-defined speed dial number(s) in response to the duress call being answered at the designated phone.

The present disclosure further contemplates that, in some embodiments, a duress call may be canceled by pressing button 64 in a predetermined sequence. The predetermined sequence for canceling the duress call may be programmable in some embodiments. For example, a long press of about two seconds, followed by a short press (e.g., about ½ second or less) of button 64 may be programmed as the call cancelation sequence for button 64 just to give one arbitrary example. Furthermore, sending a duress call signal may also be programmable, such as requiring that button 64 be pressed for a long duration, such as about three or four seconds or more, in some embodiments, as long as the button press duration and/or sequence of button 64 for placing a duress call is different than the predetermined duration and/or sequence of button press sequence of button 64 for canceling a duress call.

A synopsis of the functionality of buttons 56, 58, 60, 62, 64 of badge 10, in some embodiments, is provided below in Table 1:

TABLE 1

| Button | Function |
|---|---|
| Front (button 56) | Press to talk button to listen to a voice command for a threshold amount of time. Also serves as an action button that, when pressed, allows the user to operate badge 10 without a voice command. Its function is contextual to what is occurring on the badge 10 at a given time. |
| Top (button 64) | Configurable speed dial to a person (or persons), department, or integrated third-party system. |
| Side top (button 58) | Increases speaker volume; navigates up in the badge 10 menu. |
| Side middle (button 62) | (i) Selects whatever is highlighted in the badge menus; or (ii) Powers down the badge 10 when held for about 4 seconds (or other programmed time for powering down badge 10, which may be more or less than about 4 seconds); or (iii) Power on the badge 10 when held for about 4 seconds (or other programmed time for powering on badge 10, which may be more or less than about 4 seconds). |
| Side bottom (button 60) | Decreases speaker volume; navigates down in the badge 10 menu. |

With regard to button 56 and the accompanying information provided in Table 1, in addition to being used as a push-to-talk button, it also can be pressed to perform the most obvious function at the time it is being pressed. For example, if there is an incoming call, it is possible to press button 56 to answer the call. In this regard, button 56 is sometimes redundant to button 62 which is the button that is pressed to perform the function shown on display 46 of badge 10. That is, the function shown on display 46 is oftentimes the most obvious function at a given time. So, for example, during an incoming call, the text, "Answer call" appears on display 46 in some embodiments and the caregiver wearing or otherwise carrying badge 10 can press button 56 or button 62 to answer the call. As will be discussed in further detail below, the caregiver also can speak a wake word and the desired command (e.g., the caregiver states, "[wake word]" or "hey [wake word]" followed by "answer call" or "answer the call") to perform the same function with badge 10. Thus, the present disclosure contemplates that the caregiver has multiple options as to how to interact with badge 10 to perform some functions.

Based on the information in Table 1, it is apparent that in the given example, badge is powered down from the on state to the off state, or is powered up from the off stated to the on state, by pressing and holding button 62 for about 4 seconds. The present disclosure contemplates that when front button 56 of badge 10 is pressed and held for about 2 seconds (or some other programmed amount of time greater than or less than about 2 seconds), the following occurs: (i) an active call is placed on hold or (ii) a held call is resumed or (iii) there is a swap between a held call and an active call, if two calls exist. If brightness or volume control is the highlighted function on the menu appearing on display 46, then top button 58 needs to be held for at least a ½ second to increase the brightness or volume and, similarly, down button 60 needs to be held for at least a ½ second to decrease the brightness or volume. Otherwise, a short press of buttons 58, 50 of less than ½ second results in up or down navigation on the corresponding menu.

With continued reference to FIG. 2, an indicator light 68 is visible on front wall 20 of housing 18 to the right of speaker openings 54 near the lower right corner of housing 18. Indicator light 68 is generally circular and, in the illustrative embodiment, includes one or more light emitting diodes (LED's) that is/are operable to be illuminated in multiple colors and in various flash patterns or types as set forth below in Table 2.

TABLE 2

| Color (Function) | Flash Type | Meaning |
|---|---|---|
| Cyan | Single flash | An alert or broadcast message is incoming or occurring. |
| Cyan | Intermittent flashes | The badge 10 has (i) an incoming call or (ii) a missed call or (iii) a missed alert. |
| Green | Single flash | The badge 10 (i) is connected to the network or (ii) is listening for a command or (iii) has completed a request. |
| Magenta | Intermittent flashes | The badge 10 is not logged in. |
| Red | Intermittent flashes | Connection issue. |
| Red | Single flash | Issue or error with the badge. |
| White | Solid | The badge is powering on or off. |
| Yellow | Solid | User is in do-not-disturb mode. |

As is apparent in Table 2, indicator light 68 can be illuminated in six different colors and is either solid (i.e., continuously illuminated so as not to flash), flashes once, or is flashed intermittently to indicate different states of badge 10. If badge 10 is turned off, indicator light 68 is turned off and is not illuminated in any color. When badge 10 is turned on, indicator light 68 defaults to being illuminated solid white unless any of the other colored conditions are applicable.

Referring now to FIG. 4, a block diagram representation of circuitry 70 of badge 10 is provided. Circuitry 70 includes a main control unit (MCU) 72, referred to herein sometimes as controller 72. In the illustrative example, MCU 72 is a model no. ilMX RT685 MCU available from NXP B.V. of Eindhoven, Netherlands. Controller 72 is configured to control display 46, the microphones 48, and speaker 52. Controller 72 is also configured to detect whether any of buttons 56, 58, 60, 62, 64 have been pressed and to respond accordingly. MCU 72 includes its own processor (aka central processing unit (CPU)) and onboard memory which stores various data and software used during operation of badge 10 such as operating systems, applications, programs, libraries, databases, and drivers. The onboard memory of controller 72 includes a plurality of instructions that, when executed by the processor of controller 72, causes the processor to perform the functions described herein.

Display 46 is controlled by MCU 72 via serial peripheral interface (SPI) signals communicated over one or more SPI lines 74 as shown in FIG. 4. In addition to the onboard memory of MCU 72, circuitry 70 includes a flash memory 76 which, in the illustrative embodiment is a model no. MX25USM51345GXi00 octal flash memory chip available from Marconix International Co., Ltd. of Hsinchu, Taiwan. Flash memory 76 communicates bidirectionally with MCU 72 via flexible SPI (FLEXSPI) lines 78. Circuitry 70 of badge 10 further includes a wireless fidelity (WiFi) module 80, which in the illustrative embodiment is a model no. LBEE5QD1ZM-572 WiFi module available from Murata Manufacturing Co., Ltd. of Nagaokakyo, Kyoto, Japan. Module 80 communicates bidirectionally with controller 72 via one or more secure digital input/output (SDIO) 4-bit mode (WiFi) lines 82 and via one or more universal asynchronous receiver/transmitter (UART) Bluetooth (BT) lines 84.

WiFi module 80 is coupled to an antenna 86 via one or more antenna lines 87 for transmission and reception of 802.11x WiFi signals, such as those communicated according to the 802.11x protocol (where "x" is the revision level a, b, c, g, etc.) and for transmission and reception of Bluetooth (BT) signals communicated according to the Bluetooth protocol including BT Low Energy (BLE) communications. The messages to be transmitted via WiFi from antenna 86 are sent to module 80 from MCU 72 over lines 82 and the messages to be transmitted via Bluetooth from antenna 86 are sent to module 80 from MCU 72 over lines 84. Similarly, the WiFi messages received by antenna 86 are sent to MCU 72 from module 80 over lines 82 and the BT messages received by antenna 86 are sent to MCU 72 from module 80 over lines 84. Accordingly, a single antenna 86 is used in circuitry 70 of badge 10 for transmitting and receiving WiFi and BT messages. Thus, a time division multiplexing scheme is used by module 80 to transmit and receive WiFi messages in time slots that are different from the time slots in which BT message are transmitted and received.

WiFi messages in system 100 are considered to be "long range" communications or signals in that their communication range extends beyond any particular patient room in which badge 10 is located. WiFi communications typically have ranges of about 150 feet (about 45 meters) indoors. As noted above, "short range" communications include communications within 10 meters or less, and "long range" communications includes any communications that are longer than "short range" communications. The precise demarcation between "short range" and "long range" communications or signals in the context of system 100 is dependent upon the types of wireless communication technologies used, the power applied to any transmission antenna sending the wireless signals, etc. and, therefore, is left to the discretion of the system designer. For example, in the context of system 100, "short range" communications can be considered to include those of about 20 meters or less and "long range" communications can be considered to include those of about 20 meters or more, just to give one arbitrary example.

Still referring to FIG. 4, an amplifier (AMP) 88 is coupled to MCU 72 via one or more I2C (aka I$^2$C) lines 90 and is coupled to speaker 52 via one or more analog LINE OUT lines 92. In the illustrative example, AMP 88 is a model no. ALC1017-CGT audio compressor/decompressor (CODEC) chip available from Realtek/Advance Logic, Inc. of Hsinchu, Taiwan. Control signals, such as volume control signals, are sent from MCU 72 to AMP 88 via lines 90. Circuitry 70 further includes a switch 94 that is coupled to MCU 72 via one or more I2S (aka I$^2$S) lines 96. Digital audio signals are communicated to switch 94 from MCU 72 and then, depending upon the position or configuration of switch 94, the digital audio signals are either fed to WiFi module 80 via one or more I2S lines 98 for wireless transmission from module 80 via antenna 86, or are fed to AMP 88 via I2S lines 101 for analog output to speaker 52 via lines 92.

In some instances, digital sound signals received by module 80 from antenna 86 are communicated to MCU 72 via switch 94 and lines 96, 98 and then, in turn, are played through speaker 52 via switch 94, AMP 88, and lines 92, 96, 101. In other instances, such as for real-time voice communications, MCU is bypassed and digital sound signals received by module 80 from antenna 86 are communicated to speaker 52 via switch 94, AMP 88, and lines 92, 98, 101 without being processed by MCU 72. Thus, switch 94 has three positions or configurations; one in which lines 96 are coupled to lines 98, one in which lines 96 are coupled to lines 101, and one in which lines 98 are coupled to lines 101.

Circuitry 70 further includes a vibrator 102 that is activated by controller 72 via one or more control lines 104 to provide the caregiver with a tactile indication (i.e., vibrations) for a short period of time (e.g., about ¼ second to about 1 second) of an incoming voice call, device alert, nurse call, notification, text message, etc. Circuitry 70 still further includes a power management integrated circuit (PMIC) 106 which, in the illustrative embodiment is a model no. PCA9420BSAZ PMIC available from NXP of Eindhoven, Netherlands. PMIC 106 receives system power from battery 43. In particular, a Positive Temperature Coefficient (PTC) device 108 receives power directly from battery 43 (or multiple batteries 43 as noted above) via one or more power lines 110 and then provides power to PMIC 106 via one or more power lines 112. PTC device 108 provides short circuit protection for battery 43. Battery 43 includes one or more lithium-ion batteries in some embodiments of badge 10.

With continued reference to FIG. 4, PMIC 106 provides operating power for controller 72 via one or more power lines 114. Controller 72 is also coupled to PMIC 106 via one or more I2C lines 116. As shown in FIG. 4, the one or more power lines 112 are also coupled to a first DC-to-DC converter 118 which, in turn, provides DC power to OLED display 46. The one or more power lines 112 are further coupled to a second DC-to-DC converter 120 which, in turn, provides power to WiFi module 80, vibrator 102, and to an ultra-wideband (UWB) module 122 to be described in further detail below. Optionally, a thermistor (not shown) is disposed within a battery pack containing the one or more batteries 43 to detect battery temperature. In such embodiments, PMIC 106 operates to provide circuitry 70 with over-temperature protection.

Illustrative circuitry 70 has a serial wire debug (SWD) debut test point or port 124 that communicates with controller 72 via one or more SWD lines 126 and via one or more universal serial bus 1 (USB1) lines 128. Debug test point 124 is also coupled to UWB module 122 via SWD lines 130 and UART lines 132. UWB module is further coupled to a UART/Inter level shifter 134 via one or more logic line 136. Shifter 134 is, in turn, coupled to controller 72 via logic lines 138. Shifter 134 shifts logic level signals of 3.3 Volts (V) on the one or more lines 138 to logic level signals of 1.8 V on the one more lines 136 and vice versa. That is, controller 72 sends and receives high logic levels on lines 138 at 3.3 V whereas UWB module 122 sends and receives high logic levels on lines 136 at 1.8 V. UWB module 122 is coupled to an UWB antenna 140 via one or more antenna lines 142. In some embodiments, UWB module 122 is a model no. DWM3001C UWB module available from Qorvo, Inc. of Greensboro, North Carolina. In such embodiments, antenna 140 is integrated into the DWM3001C UWB module.

Figure 5:
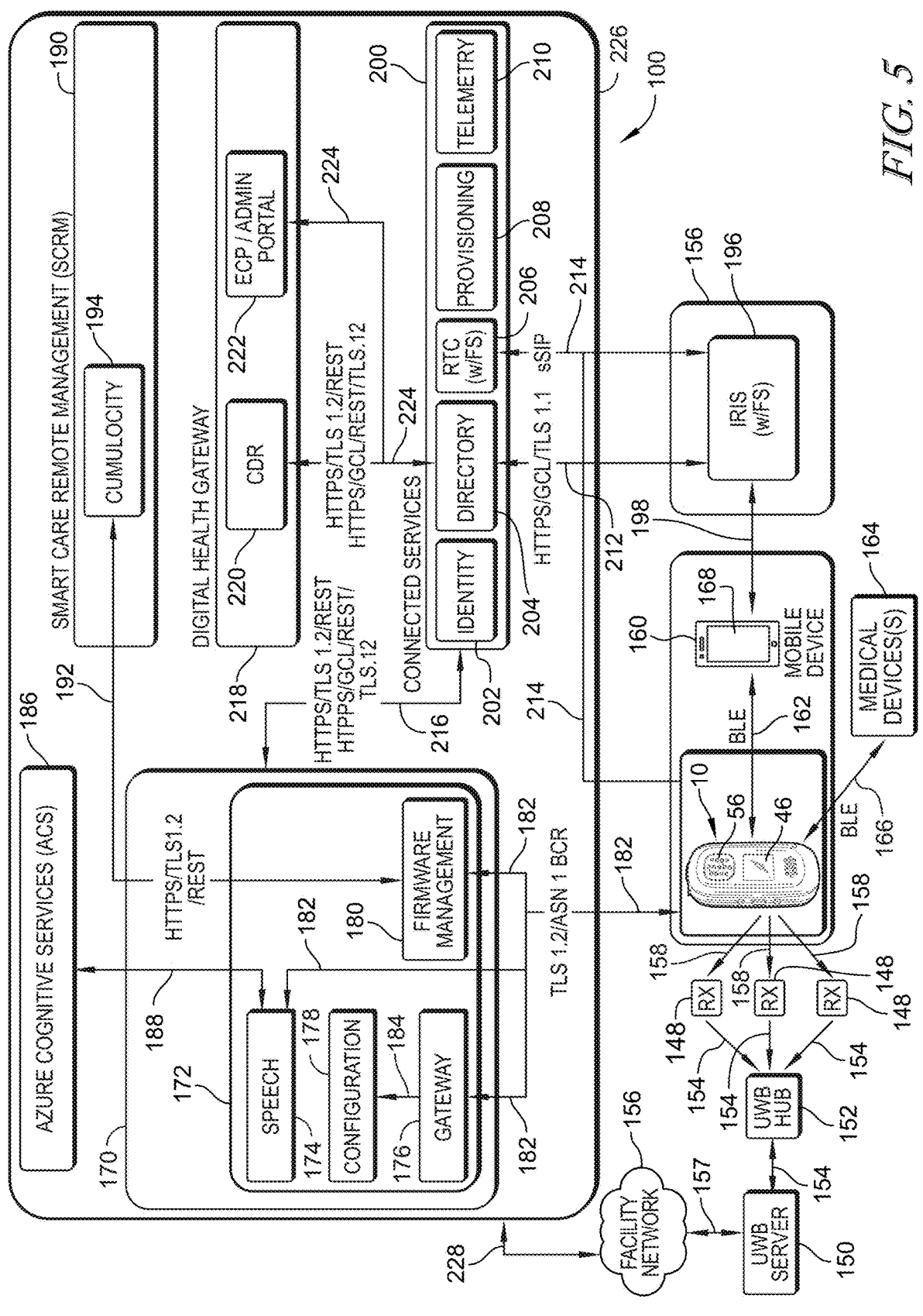
FIG. 5 is a block diagram showing a healthcare communication system in which the voice communication badge of FIGS. 1-4 is included and showing the voice communication badge communicating directly with a mobile phone of the caregiver.

According to the present disclosure, UWB module 122 operates to send periodic UWB locating signals (aka beacon signals) through antenna 140 for receipt by receivers 148 of a real-time locating system (RTLS) as shown in FIG. 5. Receivers 148 of RTLS are mounted at fixed locations throughout a healthcare facility and therefore, the receivers are sometimes referred to anchors 148. The anchors 148 are, in turn, coupled to one or more RTLS computers or servers 150 (aka UWB computers or servers 150) through other hardware, including respective UWB hubs 152 and corresponding cables or lines 154, in some embodiments. In other embodiments, hubs 152 are omitted. In the illustrative FIG. 5 example, UWB server 150 is included in, or otherwise coupled to, a network 156 of the healthcare facility as indicated by double-headed arrow 157. The architecture of the RTLS in any given healthcare facility is at the discretion of the RTLS designer. In any event, by equipping badge 10 with UWB module 122, the badge 10 serves as a locating tag in addition to serving as a voice communication device. Accordingly, caregivers that carry or wear badges 10 do not need separate locating tags.

UWB module 122 of badge 10 is operated in a manner substantially similar to the manner in which locating tags of the Hillrom Precision Locating (HPL) System are operated. Details of such operation can be found in U.S. Pat. Nos. 11,317,246 and 11,289,194 which are hereby incorporated by reference herein for all that they teach to the extent not inconsistent with the present disclosure which shall control as to any inconsistencies. Thus, UWB module 122 of badge 10 cooperates with receivers 148, UWB server 150, and hub 152, if present, to provide system 100 with a high-accuracy RTLS using UWB technology that is able to determine the location of each badge 10 that is in communication with at least three of transceivers 148 within about one foot (30.48 cm) or less of the badge's actual location. In other embodiments, the RTLS of system 100 is able to determine the location of each badge 10 that is in communication with at least three of transceivers 148 within about three feet (91.44 cm) or less of the badge's actual location and such embodiments are still considered to be high-accuracy RTLS's according to the present disclosure.

In general, UWB module 122 periodically sends a "blink" signal or message 158 (e.g., a single packet of UWB data including a badge ID) via antenna 140 that is received at multiple receivers 148, shown in FIG. 5, at slightly different times as a result of the distances between badge 10 and the various RTLS receivers 148 being different. In some embodiments, the time of arrival of the blink signal 158 at the receivers are compared (e.g., subtracted from each other) and processed to determine the location of badge 10. The locating methodologies used in the RTLS can include time-of-flight (ToF) methodologies, time-of-arrival (ToA) methodologies, time-difference-of-arrival (TDoA) methodologies, angle of arrival (AoA) methodologies, triangulation methodologies, and the like. Blink signals 158 are sometimes referred to herein as beacon signals 158. That is, terms "blink signal," "beacon signal," "blink message," and "beacon message" are used interchangeably herein.

The present disclosure further contemplates that, in variant embodiments, WiFi module 80 and UWB module 122 are combined into a single module that performs the functions of both. Modules 80 and 122 are sometimes referred to as "radios" (e.g., WiFi radio 80 and UWB radio 122) by those skilled in the art. The contemplated combined module or radio may have a single antenna that combines the functions of antennas 86, 140 discussed above, or may have separate antennas corresponding to antennas 86, 140 such that one is used for WiFi communications and the other is used for UWB communication. If a single antenna is used in the combined radio, then a time slicing (aka time division multiplexing) is implemented to alternate between sending WiFi signals, sending UWB signals, receiving WiFi signals, and/or receiving UWB signals. If separate WiFi and UWB are used in the combined radio, then the separate antenna may be used concurrently for sending/receiving respective WiFi and UWB signals.

As also shown in FIG. 4, each illustrative microphone 48 of circuitry 70 is a digital microphone (DMIC) that receives spoken analog inputs and converts them to Pulse Density Modulation (PDM) digital outputs which are communicated to controller 72 on one or more PDM lines 144. Each of buttons 56, 58, 60, 62, 64 is coupled to controller 72 via respective input lines 146 and indicator light 68 is coupled to controller 72 via one or more output lines 147 as further shown in FIG. 4. Thus, controller 72 senses incoming signals on lines 146 whenever any of buttons 56, 58, 60, 62, 64 are pressed and responds accordingly. Controller 72 also sends signals on the one or more lines 147 to control the illumination of indicator light 68 as described above.

According to the present disclosure, badge 10 meets the IP54 ingress standard for protection against dust and fluid ingress (e.g., fluid splashes) with healthcare grade plastics material being used for housing 18 of badge 10 to allow frequent cleaning of housing 18 with disinfecting chemical solutions. Additional details of badge 10 are shown and described in U.S. Patent Application Publication No. 2023/0195866 A1 which is hereby incorporated by reference herein in its entirety for all that it discloses to the extent not inconsistent with the present disclosure which shall control as to any inconsistencies.

In some uses of badge 10, the caregiver may grab badge 10 and flip it by about 90 degrees to about 180 degrees from the orientation shown in FIG. 1 while the badge 10 is still clipped to the caregiver's clothing or worn on a lanyard or necklace so that the caregiver can look at the front of badge 10. In such orientations of badge 10, the bottom of badge 10 is at an elevation that is generally equal to, or above (e.g., higher in elevation than), the top of badge 10. The present disclosure contemplates that when badge 10 is re-oriented by the caregiver in this manner, the information appearing on screen 46 of badge 10 flips by 180 degrees so that the information appears in a right-side-up orientation on screen 46 as viewed by the caregiver. Thus, in some embodiments, badge 10 includes an orientation sensor such as an accelerometer, a ball switch, a mercury switch, a liquid gage, or the like that is coupled to controller 72 to determine whether badge 10 is in the regular, upright orientation shown in FIGS. 1-3, or is tilted or flipped for viewing by the caregiver. In this regard, see, for example, accelerometer 174 in U.S. Patent Application Publication No. 2024/0163604 which is hereby incorporated by reference herein for all that it teaches to the extent not inconsistent with the present disclosure which shall control as to all inconsistencies. In some embodiments of badge 10 having the 180-degree flip of the information on screen 46, the functionality of buttons 58, 60 are swapped or reversed during the 180 degree screen flip. For example, during the screen flip, button 60 is used to increase the speaker volume and button 58 is used to decrease the speaker volume, just to give one scenario.

Referring now to FIG. 5, additional details of exemplary healthcare communication system 100 are shown diagrammatically. In addition to wearing or carrying badge 10, the caregiver further carries a mobile device 160 such as the illustrative mobile phone. Thus, device 160 is sometimes referred to as phone 160 herein. The term "mobile phone" as used herein includes, but is not limited to, handheld smartphones and handheld tablets having voice communication capability. As noted above, badge 10 includes module 80 that cooperates with controller 72 to provide badge 10 with Bluetooth communication capability. In this regard, badge 10 pairs with mobile device 160 for Bluetooth Low Energy (BLE) communications therebetween in some embodiments as indicated by double-headed arrow 162 in FIG. 5. Badge 10 also communicates with any medical devices 164 that are within BLE communication range (e.g., "short range" communication such as 10 meters (32 feet) or less) as indicated by double-headed arrow 166 in FIG. 5. In some embodiments, badge 10 uses signal strength values of incoming BLE messages to limit communications with only those devices (e.g., mobile phone 160 and medical devices 164) that are much closer in range than 10 meters, such as devices 160, 164 that are only within about 1 meter (3 feet) to about 3 meters (10 feet) of badge 10, for example. This serves to limit the number of devices 160, 164 with which badge 10 communicates so that medical devices 164 that are likely to be located in other rooms of a healthcare facility, as well as mobile devices 160 of other caregivers, do not establish BLE communications with badge 10.

The present disclosure contemplates that both badge 10 and mobile phone 160 of the caregiver receive alert messages such as nurse calls, medical device alerts, text messages, phone or voice calls, and so forth. Thus, the caregiver has the option of accepting or answering the message or call on either badge 10 or phone 160. If the caregiver accepts the message or call using badge 10, then badge 10 sends a BLE notification message to phone 160 in that regard and the status of the incoming message or call is updated in mobile phone 160. Similarly, if the caregiver accepts the message or call using mobile phone 160, then phone 160 sends a BLE notification message to badge 10 in that regard and the status of the incoming message or call is updated in badge 10.

In other embodiments, badge 10 does not pair with mobile phone 164 such that BLE link 162 is not present in system 100. In such embodiments, a database at a remote computer, such as one or more servers discussed below, maintains an association list of each caregiver's badge ID and mobile phone ID. Thus, acceptance of an alert message or other message or call on badge 10 results in the remote computer sending a message regarding the acceptance to the mobile phone 160 of the associated caregiver which results in the status of the incoming message or call being updated in mobile phone 160. Similarly, acceptance of an alert message or other message or call on mobile phone 160 results in the remote computer sending a message regarding the acceptance to the badge 10 of the associated caregiver which results in the status of the incoming message or call being updated in badge 100. In each of the foregoing embodiments in which status updates are coordinated between badge 10 and phone 160, the updating of messages and calls by badge 10 or phone 160, based on inputs occurring on the other of badge 10 or phone 160, may result in information on respective displays 46, 168 being altered if the respective display 46, 168 is showing pertinent information at the time of updating, or may simply result in information in memory of the badge 10 or phone 160 being updated with the new status information for possible display at a later time, as appropriate.

Based on the foregoing, it should be appreciated that, under some circumstances, a menu or list of calls and messages appearing on display 46 of badge 10 and on a display 168 of phone 160 are both altered to indicate the acceptance/answered status of the message or call, as the case may be, regardless of whether the message or call is accepted/answered using badge 10 or using phone 160. In other words, communications 162 between badge 10 and phone 160 via BLE link 162 or via one or more remote computers of system 100, are used to coordinate call/message status, display of menus, and other functions that are common to badge 10 and phone 160. For example, if a voice call is answered on badge 10, then phone 160 will stop ringing. On the other hand, if a voice call is answered on phone 160, the badge 10 will stop vibrating. As another example, a status indicated by indicator light 68 of badge 10 may be shown on display 168 of phone 160 as a textual message or as some other visual indicia including an emulation of the indicator light 68 itself. Of course, a similar text message corresponding to the status of indicator light 68 may be shown on display 46 of badge 10 in some embodiments. Similarly, the manner in which indicator light 68 is illuminated on badge 10 is altered, as appropriate, in response to inputs entered on display 168 of phone 160. For example, if inputs on phone 160 are made by the caregiver to enter into the do not disturb status, then indicator light 68 is illuminated amber or yellow on badge 10. Do not disturb status is used, for example, when a caregiver is busy in a manner that prevents them from receiving any further calls or alerts.

With regard to BLE communications 166 between badge 10 and one or more medical devices 164, these can be used by the RTLS, which includes receivers 148, UWB server 150 (aka RTLS server 150) and, in some embodiments, UWB hub 152, to determine the location of medical devices 164 that otherwise do not have locating tags attached thereto. In particular, when badge 10 is determined by the RTLS to be located in a particular room of a healthcare facility, then any of medical devices 164 that communicate with badge 10 via wireless BLE communication links 166 can also be designated by RTLS server 150 as being located in the same room as badge 10. To accomplish this, medical devices 164 transmit medical device ID's to badge 10 for forwarding to receivers 148. Thus, the medical device ID's are included in the blink or beacon messages 158 along with the badge ID. For example, in some embodiments, the blink messages 159 each include the ID of badge 10 and the ID's of the one more medical devices 164 located in the same room as badge 10, or alternatively, separate beacon messages can be transmitted from UWB module 122 of badge 10 via antenna 140 with the ID of badge 10 in one beacon message and the ID's of each respective medical device 164 in the room in corresponding separate, distinct beacon messages. Of course, the blink or beacon message sequence repeats periodically (e.g., about every 10 seconds, or about every 30 seconds, or about every minute, just to give a few examples).

Based on the foregoing, the present disclosure contemplates that badge 10 serves as a mobile or roving locator unit such that, as badge 10 moves from room-to-room throughout a healthcare facility, different medical devices 164 establish BLE communication links 166 with badge 10 in each room and then RTLS server 150 associates the medical devices 164 with the particular room based on BLE communications 166 between badge 10 and medical devices 164 in each particular room. In some embodiments, information regarding the medical devices 164 that are within BLE communication range of badge 10 are listed on display 46 of badge 10 and then the caregiver uses buttons 58, 60, 62 to select which of the listed medical devices 164 are actually located within the same room as the caregiver, thereby to initiate device-to-room association in the RTLS server 150 with only the proper devices 164. Thus, medical devices 164 in other rooms are not selected by the caregiver, or alternatively are de-selected, by the caregiver using badge 10.

Alternatively or additionally, the medical devices 164 that are within BLE communication range of badge 10 are listed on display 168 of mobile phone 160 and then the caregiver provides inputs on display 168 to select which of the listed medical devices 164 are actually located within the same room as the caregiver, thereby to initiate device-to-room association in the RTLS server 150 with only the proper devices 164. Thus, medical devices 164 in other rooms are not selected, or alternatively are de-selected, by the caregiver using mobile phone 160. In such embodiments, information regarding the medical devices 164 in communication with badge 10 via BLE communication links 166 is transmitted to mobile phone 160 from badge 10 via BLE communication link 162.

In some embodiments of system 100, after one or more medical devices 164 are associated with a particular room by RTLS server 150 at a first time in response to appropriate inputs by a caregiver using badge 10 and/or phone 160, if the caregiver leaves the room and then comes back into the room at a later time (e.g., 15 minutes later, an hour later, a day later, etc.) and if one or more of the medical devices 164 that were previously associated with the room by RTLS server 150 are no longer detected by badge 10 after the caregiver's return to the room, the RTLS server 150 initiates a message for display on display 46 of badge 10 and/or on display 168 of phone 160 so that the caregiver can confirm that the previously associated medical device 164 is no longer present in the room.

Furthermore, after a caregiver uses badge 10 and/or phone 160 to associate one or more medical devices 164 with a particular room at a first time, then the caregiver is not prompted to make inputs on badge 10 and/or mobile phone 160 at later times to re-associate medical devices 164 with the room if they are detected once again by badge 10 via BLE communications 166. The same goes for other caregivers that enter the particular room with their respective badge 10 and/or phone 260 after the first caregiver has confirmed the association of the one or more medical devices 164 with the room using the first caregiver's badge 10 and/or phone 160. However, if one or more of the medical devices 164 that were previously associated with the room based on BLE communications 166 with a first caregiver's badge 10 are not detected by a second caregiver's badge 10 after the second caregiver enters the room, the RTLS server 150 initiates a message for display on display 46 of badge 10 and/or on display 168 of phone 160 of the second caregiver so that the second caregiver can confirm that the previously associated medical device 164 is no longer present in the room.

The present disclosure also contemplates that in some embodiments of system 100, previously made device-to-room associations using badge 10 and/or phone 160 will expire automatically after some predetermined amount of time (e.g., after each work shift, or after about 24 hours, or after about one week, just to give a few examples). In such embodiments, a new device-to-room association will need to be made by a caregiver for each medical device 164 that is still present in the particular room using badge 10 and/or phone 160 as described above. Furthermore, if a particular medical device 164 has been associated with a first room by use of badge 10 and/or phone 164 and then the particular medical device 164 becomes associated with a second room at a later time, the particular medical device 164 will automatically become disassociated with the first room by RTLS server 150.

With continued reference to FIG. 5, system 100 includes a badge communication server 170 having a suite 172 of badge communication applications or software modules. In the illustrative embodiment, suite 172 includes a speech module 174, a gateway module 176, a configuration module 178, and a firmware management module 180. Badge 10 communicates messages to modules 174, 176, 180 according to the Transport Layer Security (TLS) version 1.2 protocol/Abstract Sequence Notation 1 (ASN 1) Basic Encoding Rules (BER) as indicated by arrows 182. The messages indicated by arrows 182 are sent wirelessly from badge 10 to wireless access points (WAP's) of network 156 and are communicated by infrastructure of network 156 to server 170. Thus, arrows 182 are intended to diagrammatically represent such WAP's and other infrastructure (e.g., cables, routers, gateways, other servers, VoIP switches, etc.) of network 156 of the corresponding healthcare facility.

Gateway module 176 is connected to configuration module 178 as indicated diagrammatically in FIG. 5 by arrow 184. Configuration module 178 is used to set up connectivity between gateway module 176 and network 156. As indicated by arrow 188, speech module 174 of server 172 receives spoken messages from badge 10 and forwards one or more message files corresponding to the spoken messages to a remote server or remote server cluster 186 for further processing using a large language model (LLM) with retrieval augmented generation (RAG). Server 186 or server cluster 186 interprets the content of the spoken messages contained in the one or more message files and responds back to speech module 172 with the results of the processing. For example, if the spoken message is "call doctor Smith," then server 186 responds to speech module 174 with a phone number or badge number of Dr. Smith that is to be called. If further information is needed, such as to identify which Dr. Smith is intended if there is more than one doctor with the last name "Smith," then the response to speech module 174 from server 186 incudes a query for further information, which query is ultimately shown on display 46 of badge 10 for answering by the caregiver. In the illustrative embodiment, server 186 (or server cluster 186) is an Azure Cognitive Services server (or server cluster) operated by Microsoft Corporation of Redmond, Washington.

Still referring to FIG. 5, firmware management module 180 is communicatively coupled to a remote management server 190 as indicated by arrow 192. Arrow 192 represents Internet infrastructure, for example. In FIG. 5, server 190 is labeled as Smart Care Remote Management (SCRM) and the communications between server 190 and module 180 of server 172 are according to one or more of the Hypertext Transfer Protocol Secure (HTTPS)/TLS 1.2/REpresentational State Transfer (REST) protocol(s). Furthermore, server 190 interfaces with module 180 of server 172 using an application management module 194 which in the illustrative example is the CUMULOCITY™ Internet-of-Things (IoT) platform. Module 194 is used to upgrade the firmware (e.g., to replace existing firmware versions with new firmware versions) of modules 174, 176, 178, 180 of server 172 and of badges 10 of system 100.

Mobile devices 160 of system 100 communicate with an Information Repository and Intelligence Service (IRIS) server 196, with file system (w/ FS), as indicated by double headed arrows 198 in FIG. 5. Although IRIS server 196 is shown as a separate block in FIG. 5, it is included as part of network 156 of the healthcare facility and so, a diagrammatic box denoted by reference number 156 surrounds server 196 in FIG. 5. IRIS server communicates with one or more connected services servers 200 as will be described in further detail below. Server 200 includes an identity application or module 202, a directory application or module 204, a Real-Time Communications (RTC) (w/ FS) application or module 206, a provisioning application or module 208, and a telemetry application or module 210.

Identity module 202 is used to input the names, ID's, and other information of the personnel of the healthcare facility that may be contacted by users of system 100 via their badges 10 and/or mobile phones 160. Directory module 204 contains contact information, such as phone numbers and badge numbers or ID's, for other healthcare facility staff and medical personnel that caregivers are able to contact (e.g., call or text) using their respective badge 10 and/or phone 160. RTC module 206 facilitates real-time voice communications between badges 10 and phones 160. Provisioning module 208 permits administrators of system 100 to manage user and application accounts, as well as credential changes and authorizations to gain access to other applications of system 100. Telemetry module 210 permits remote monitoring of the health, security, and performance of other modules, software applications, and application components of system 100, including monitoring in real time in some embodiments.

IRIS server 196 communicates with directory module 204 of server 200 according to one or more of the HTTPS/ Generic Communication Layer (GCL)/Transport Layer Security (TLS) version 1.1 protocols as indicated by double-headed arrow 212 in FIG. 5. IRIS server 196 and badge 10 also each communicate with RTC module 206 according to the simple Session Initiation Protocol (sSIP) as indicated by double headed arrows 214 in FIG. 5. Furthermore, server 200 communicates with server 170 according to one or more of the HTTPS/TLS 1.2/REST and/or HTTPS/GCL/REST/ TLS. 12 protocols as indicated by double-headed arrow 216.

With continued reference to FIG. 5, system 100 further includes a digital health gateway 218 such as the Digital Health Platform available from Baxter International, Inc. of Deerfield, Illinois, U.S.A. Gateway 218 is a server in some embodiments and includes a clinical data repository (CDR) 220 for storage of clinical data. Thus, CDR 220 is provided by memory of gateway 218 in the illustrative example of system 100. Gateway 218 also includes an Exchange Control Panel (ECP)/Admin portal 222. Directory module 204 of server 200 communicates with each of CDR 220 and ECP/Admin portal 222 according to one or more of the HTTPS/TLS 1.2/REST and/or HTTPS/GCL/REST/TLS. 12 protocols as indicated by double-headed arrow 224. Portal 222 has auditing functionality regarding usage of badges 10 in system 100 so that audit reports are exportable to other computer devices of system 100. Device management, status, and metrics of badges 10 are also accessible within portal 222, as is facility management of badges 10 (e.g., configuration, device registration/deregistration, and establishment of staff and non-staff contacts for badges 10).

A diagrammatic box 226 is shown in FIG. 5 and surrounds portions of system 100 that are located outside of the healthcare facility and that are operated by one or more other parties. For example, in some embodiments of system 100 servers 170, 190, 200, 218 are operated by Baxter International, Inc. and server 186 (or server cluster 186) is operated by Microsoft Corporation. The services performed by the computer devices within diagrammatic box 226 of FIG. 5 may be considered to be cloud-based services according to the present disclosure. In some embodiments of system 100, other devices within facility network 156 are in communication with the such cloud-based services via Internet infrastructure as indicated by double-headed arrow 228. It should be understood that each of double-headed arrows 157, 162, 166, 182, 188, 192, 198, 212, 214, 216, 224, 228 in FIG. 5 diagrammatically represents bidirectional communications between the devices, modules, applications, or other portions of system 100 interconnected by such double-headed arrows.

As noted above, badge 10 includes voice command button 56 (aka push-to-talk button 56) that is pressed by the caregiver to activate or turn on microphones 48 for a period of time, such as about 10 seconds or some other amount of time, to receive the caregiver's spoken commands. The present disclosure further contemplates that, as an alternative to pressing button 56, one or more spoken wake words will also result in microphones 48 being activated or turned on for the designated period of time. In this regard, the controller 72 of badge 10, even in sleep mode, is powered sufficiently to determine whether any of the one or more wake words have been spoken by the caregiver wearing badge 10. In the discussion that follows, the wake word used for badge 10 is "Scotty." When the wake word is detected, circuitry 70 of badge 10 is fully powered up from the sleep state and listens for spoken commands from the caregiver using microphone 48. Of course, pressing any of buttons 56, 58, 60, 62, 64 also wakes circuitry 70 of badge 10 from the sleep mode so that the circuitry 70 operates according to the particular button press.

The tables which follow provide examples of the types of spoken commands that cause specific functions to be performed after circuitry 70 of badge 10 has been woken from the sleep state by pressing button 56 or via use of the wake word, "Scotty." In the list of voice commands in the tables that follow, if button 56 has been pressed by the user, then it is not necessary for the user to also state, "Hey Scotty" but instead, the user just needs to speak the remaining portion of the given command. Of course, the user also can state "Hey Scotty" after button 56 is pressed, but it is simply redundant to the press of button 56. It should be appreciated that the examples given in the following tables are not intended to be exhaustive and that other spoken commands may be used with a similar result. Furthermore, it should be appreciated that ACS system 186 receives the spoken voice commands from badge 10, processes the voice commands for meaning, and then returns a digital message, such as a text string, setting forth the particular function to be performed by badge 10. Depending upon the content of the text string received from ACS system 186, gateway 176 and/or module 180 of server 172 180 may perform further processing or interpretation of the text string prior to sending an output message to badge 10. Additionally, there are some text strings returned from ACS system 186 that are processed locally within badge 10 by controller 72 to control physical attributes of badge 10, such as the volume of speaker 52 and/or the brightness of display 46.

Table 3 below provides examples of voice commands that may be spoken by caregivers to log into badge 10 or to log out of badge 10:

TABLE 3

| Workflow | Command |
| --- | --- |
| Log in | "Hey Scotty, log me in" |
| | "Hey Scotty, sign me in" |
| Log out | "Hey Scotty, log me out" |
| | "Hey Scotty, sign me out" |

Table 4 below provides examples of voice commands that may be spoken by caregivers into badge 10 to place and answer voice calls using badge 10:

TABLE 4

| Workflow | Command |
| --- | --- |
| Place a call | "Hey Scotty, call . . . " |
| | "Hey Scotty, dial . . . " |
| | "Hey Scotty, phone . . . " |
| | "Hey Scotty, ring . . . " |
| | "Hey Scotty, contact . . . " |
| Answer a call | "Hey Scotty, answer" |
| | "Hey Scotty, pick up" |
| Decline a call | "Hey Scotty, decline" |
| | "Hey Scotty, answer" |
| | "Hey Scotty, ignore" |
| End a call | "Hey Scotty, hang up" |
| | "Hey Scotty, end" |
| | "Hey Scotty, close" |
| | "Hey Scotty, terminate" |
| | "Hey Scotty, stop" |
| | "Hey Scotty, quit" |
| | "Hey Scotty, cancel" |
| Place a call on hold | "Hey Scotty, hold" |
| | "Hey Scotty, put on hold" |
| Resume a call placed on hold | "Hey Scotty, resume" |
| | "Hey Scotty, restart" |
| | "Hey Scotty, turn off hold" |
| | "Hey Scotty, unhold" |
| Swap between a held call and an active call | "Hey Scotty, change" |
| | "Hey Scotty, switch" |
| | "Hey Scotty, swap" |
| | "Hey Scotty, toggle" |

Table 5 below provides examples of voice commands that may be spoken by caregivers into badge 10 with regard to handling communication history information using badge 10:

TABLE 5

| Workflow | Command |
| --- | --- |
| List alert history | "Hey Scotty, List missed alert(s)" |
| | "Hey Scotty, List last alert" |
| | "Hey Scotty, List the room number for the alert" |
| | "Hey Scotty, Accept the alert" |
| | "Hey Scotty, Respond to the alert" |
| List broadcast history | "Hey Scotty, list missed broadcast(s)" |
| | "Hey Scotty, list last broadcast" |
| | "Hey Scotty, list who broadcast" |
| | "Hey Scotty, list most recent broadcast" |
| List call history | "Hey Scotty, list missed call(s)" |
| | "Hey Scotty, list last call" |
| | "Hey Scotty, list who called" |
| | "Hey Scotty, list most recent call" |
| List notification history | "Hey Scotty, List missed notification(s)" |
| | "Hey Scotty, List last notification" |
| | "Hey Scotty, List the room number for the notification" |
| | "Hey Scotty, Accept the notification" |
| | "Hey Scotty, Respond to the notification" |

Table 6 below provides examples of voice commands that may be spoken by caregivers into badge 10 with regard to initiating broadcast messages using badge 10:

TABLE 6

| Workflow | Command |
| --- | --- |
| Initiate a broadcast | "Hey Scotty, start a broadcast" |
| | "Hey Scotty, start a broadcast message" |
| | "Hey Scotty, send a broadcast" |
| | "Hey Scotty, send a broadcast message" |

With regard to broadcast messages, the present disclosure contemplates that badge 10 is configurable to send broadcast messages to a select number of other badges 10 (e.g., 1-500 other badges 10) or other designated endpoints (e.g., mobile devices 160, hardwired phones, room stations, staff stations, master nurse stations, pillow speaker units, etc.). Broadcast messages received by badges 10 are retained for about one hour in some embodiments for later playback. However, in other embodiments, broadcast messages received by badges 10 are retained for an amount on time that is greater than or less than one hour.

Table 7 below provides examples of voice commands that may be spoken by caregivers into badge 10 with regard to initiating and ending the do-not-disturb (DND) feature of badge 10:

TABLE 7

| Workflow | Command |
| --- | --- |
| Initiate Do Not Disturb (DND) | "Hey Scotty, Do not disturb" |
| | "Hey Scotty, DND" |
| | "Hey Scotty, start do not disturb" |
| | "Hey Scotty, start DND" |
| | "Hey Scotty, do not disturb on" |
| | "Hey Scotty, DND on" |
| | "Hey Scotty, activate do not disturb" |
| End Do Not Disturb (DND) | "Hey Scotty, end do not disturb" |
| | "Hey Scotty, end DND" |
| | "Hey Scotty, do not disturb off" |
| | "Hey Scotty, DND off" |
| | "Hey Scotty, deactivate do not disturb" |

Table 8 below provides examples of voice commands that may be spoken by caregivers into badge 10 with regard to adjusting a brightness of display 46 of badge 10:

TABLE 8

| Workflow | Command |
| --- | --- |
| Increase the brightness of the screen | "Hey Scotty, brightness up" |
| | "Hey Scotty, brightness high" |
| | "Hey Scotty, brightness medium" |
| Decrease the brightness of the screen | "Hey Scotty, brightness down" |
| | "Hey Scotty, brightness low" |
| | "Hey Scotty, brightness medium" |

Table 9 below provides examples of voice commands that may be spoken by caregivers into badge 10 with regard to adjusting a volume of speaker 52 of badge 10:

TABLE 9

| Workflow | Command |
| --- | --- |
| Increase the volume of the badge | "Hey Scotty, volume up" |
| | "Hey Scotty, sound up" |
| | "Hey Scotty, sound (1-10)" |
| Decrease the volume of the badge | "Hey Scotty, volume down" |
| | "Hey Scotty, sound down" |
| | "Hey Scotty, sound (1-10)" |

With regard to the portion of commands having "(1-10)" in Table 9, it should be understood that the user selects any number between 1 and 10 to represent the desired volume and states just that single number as part of the voice command. Thus, volume levels between 1 (lowest volume) and 10 (highest volume) are contemplated by the present disclosure. Other gradations of volume, such as low, medium, and high, or numerical gradations of 1-100, may be used in other embodiments, just to give a couple of examples.

If an interaction with badge 10 is ongoing, such as when badge 10 is still in active listening mode after having been woken up by previous use of a wake word (e.g., "Scotty" in the illustrative examples), then the wake word does not need to be re-stated in connection with subsequent voice commands. Table 10 below provides examples of voice commands that may be spoken by caregivers into badge 10 to cancel an interaction with badge 10:

TABLE 10

| Workflow | Command |
| --- | --- |
| Cancel an interaction | "Stop" |
| | "Shut up" |
| | "Quit" |
| | "Cancel" |
| | "Terminate" |
| | "Never mind" |

Table 11 below provides examples of variations of yes and no responses that may be spoken into badge 10 by caregivers with regard to queries announced to the caregiver from badge 10:

TABLE 11

| Workflow | Command |
| --- | --- |
| Yes | "Yes" |
| | "Yup" |
| | "Right" |
| | "Correct" |
| | "True" |
| No | "No" |
| | "Nope" |

TABLE 11-continued

| Workflow | Command |
|---|---|
| | "Wrong" |
| | "Negative" |
| | "False" |

Table 12 below provides examples of text that may appear on display 46 of badge 10 in connection with navigating through an associated menu of badge 10 using buttons 58, 60, 62:

TABLE 12

| Menu Item | Function |
|---|---|
| Home | When selected, returns you to the Home screen |
| Alerts | When selected, lists any received alerts |
| Calls | When selected, lists any received calls |
| Settings | From the Settings menu, you can do the following |
| | Adjust the display brightness |
| | Set your Do Not Disturb status |
| | Adjust the badge volume |
| System Info | From the System Info menu, you can view the following in the sub menus: |
| | Device: |
| | Serial Number |
| | Memory Usage |
| | Part Number |
| | Current Data |
| | Domain |
| | Firmware: Shows current firmware |
| | Locating: Lists Badge ID to be used with the RTLS |
| | Network: |
| | SSID |
| | IP Address |
| | MAC Address; Security |
| | Timers: Shows the Total Operating Time and the Up Time |
| Power Off | When selected, powers off the badge |

As discussed above, badge 10 includes a vibrator 102 that is activated by controller 72 to provide the caregiver with a tactile indication (i.e., vibrations) regarding various activities occurring on badge 10 such as an incoming voice call, device alert, nurse call, notification, text message, etc. In some embodiments, a tone is also emitted from speaker 52 whenever vibrator 102 is vibrating. Table 13 below provides information regarding the various vibration and tone patterns of badge 10 in this regard:

TABLE 13

| Tone + Haptic Name | Vibration Pattern |
|---|---|
| Listening | Single |
| Completed (connected, done) | Single |
| Error | Short + Long |
| Alert - High | Triple |
| Alert - Medium or Low | Double |
| Ring Tone - Outgoing | Double |
| Ring Tone - Incoming | Double |
| Call Waiting | Double |
| Audio Open | Double |
| Audio Closed | Double |
| Call on Hold - Holder | Single, intermittent |
| Call on Hold - Holdee | Single, intermittent |
| Power On | Chime |
| Logged In | Single |
| Broadcast Message | Triple |
| Working, reconnecting | None |
| Power Down | Short + Long |
| Volume | Single |

Figure 6:
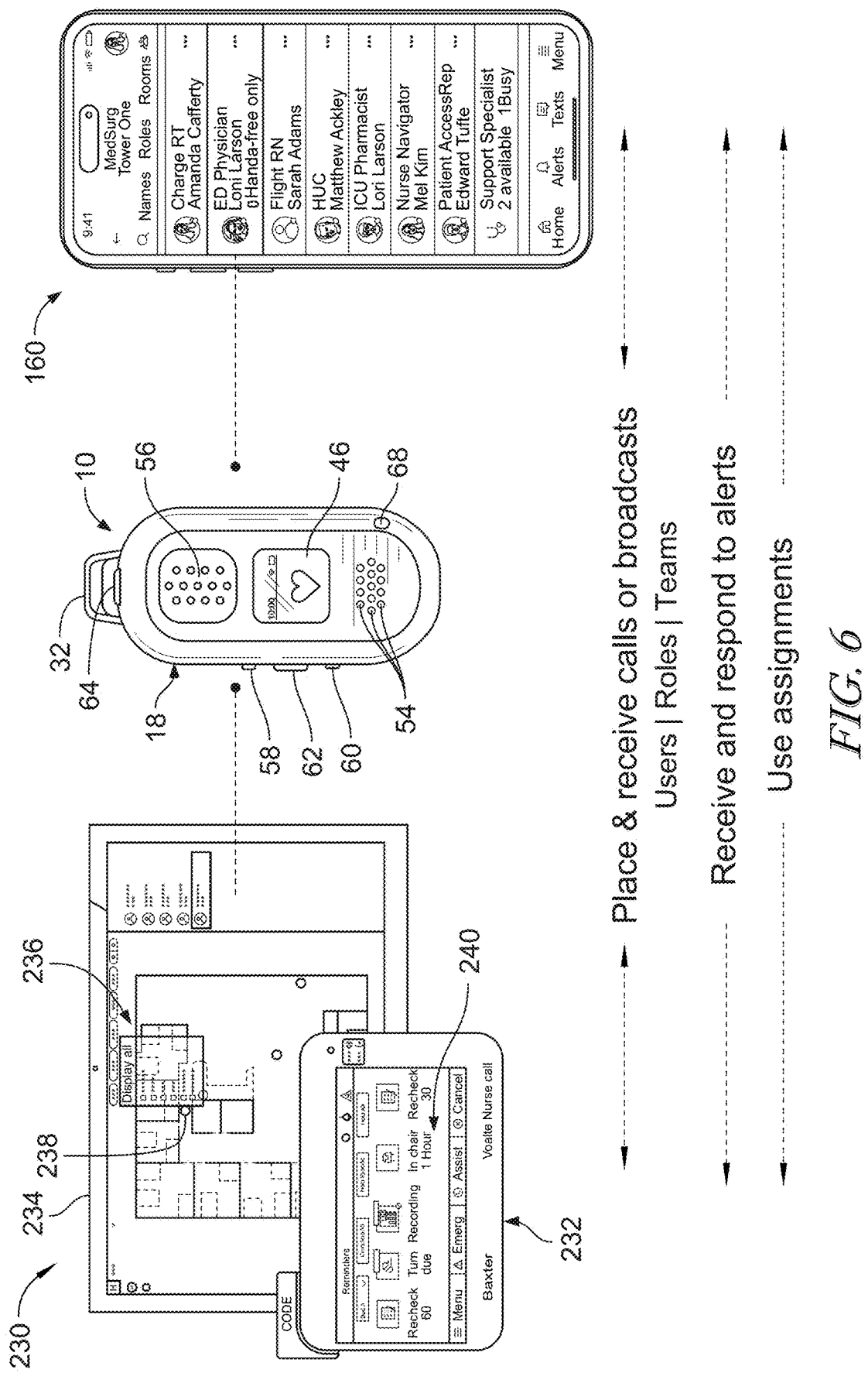
FIG. 6 is a diagrammatic view showing that the communication badge of FIGS. 1-5 is operable to communicate with a computer of a locating and tracking system, a graphical room station of a nurse call system, and a mobile phone of a caregiver.

Referring now to FIG. 6, a diagrammatic view is provided showing that the communication badges 10 of system 100 are operable to communicate with a computer 230 of the RTLS of the type that was discussed hereinabove. Accordingly, computer 230 is communicatively coupled to server 150, for example. FIG. 6 also shows diagrammatically that badges 10 of system 100 are operable to communicate with a graphical room station 232 of a nurse call system. In the illustrative example, room station 232 is of the type included in the VOALTE® Nurse Call System available from Baxter International, Inc. of Deerfield, IL, U.S.A. Additional details of such a suitable nurse call system for inclusion in system 100 can be found, for example, in U.S. Pat. Nos. 5,561,412; 5,838,223; 7,319,386; 7,538,659; 8,046,625; 8,169,304; 8,384,526; 8,598,995; and 8,779,924, each of which is hereby incorporated by reference herein to the extent not inconsistent with the present disclosure which shall control as to any inconsistencies.

FIG. 6 further shows diagrammatically that badges 10 of system 10 are operable to communicate with mobile devices 160, illustratively a mobile phone, of a caregiver. The present disclosure contemplates a simultaneous login feature in which logging into badge 10 also initiates a login of the caregiver, or other user, into a communication and alert handling application on their associated mobile device 160, if the respective mobile device 160 is associated with badge 10 such as via a common caregiver ID, for example, or via other association information such as a badge-to-mobile device association stored in portal 222 and/or in connected services server 200. One example of such a suitable communication and alert handling application is the VOALTE® Mobile application available from Baxter International, Inc. of Deerfield, IL, U.S.A. Further details of a suitable communication and alert handling application can be found in U.S. Pat. No. 11,257,588 which is hereby incorporated by reference herein in its entirety to the extent not inconsistent with the present disclosure which shall control as to any inconsistencies. Also according to the simultaneous login feature, if the caregiver or other user logs into the communication and alert handling application of their mobile device 160, a login of the caregiver, or other user, into their respective badge 10 is also initiated, if there is an association between the mobile device 160 and the respective badge 10, such as in any of the manners just mentioned.

In some embodiments, logging into badge 10 and/or the communication and alert handling application of mobile device 160, requires that the user provides an authorized user name and password, either via entry of text such as on mobile device 160 or via spoken commands to badge 10. An arbitrary example of logging in by voice in such embodiments is, for example, "hey Scotty, log in nurse Johnson having pin 1234." Providing the authorized user ID and password via either badge 10 or mobile device 160, results in logging in to both devices without the need to enter the user ID and password a second time on the other device. The simultaneous login feature is dependent upon badge 10 and mobile device 160 being in proximity, such as by having an established BLE link 162 therebetween, in some embodiments. Of course, users are also able to individually and separately login to their badge 10 and mobile device 160. For example, a caregiver may login to the communication and alert handling application on their mobile device 160 when first arriving at work while eating breakfast in a cafeteria and then later log in to badge 10 after picking up their badge 10 once they arrive at a master nurse station of their nursing unit.

A display screen 234 of computer 230 of the RTLS displays a floor plan 236, or other similar healthcare facility map, on which locations of badges 10 are shown with corresponding location icons 238 as shown in FIG. 6. In some embodiments, location icons 238 vary depending upon the status of badge 10 (e.g., currently being used for voice communication, duress call has been placed, currently located in a patient room from which an alert or nurse call has been sent and not yet cleared, caregiver also has a mobile device 160 that is associated with badge 10, etc.). For example, color coding is used for location icons 238 and/or the shape of location icons 238 is used to indicate the status of badge 10.

Graphical room station 232 (aka GRS 232), which is sometimes also referred to as a graphical audio station (GAS), has a touchscreen display 240 which is used by caregivers to view tasks and alerts and to provide inputs to the associated nurse call system regarding completion of tasks and clearing of alerts. For example, inputs on display 240 are used to indicate completion of rounds or completion of a patient turn of a corresponding patient on the respective patient bed 164. The present disclosure contemplates that use of touchscreen 240 by caregivers regarding task completion or alert rectification are communicated to badge 10 and mobile device 160 of assigned caregivers to adjust task lists and alert response statuses in these respective devices. In this regard, the nurse call system of which GRS 232 is a part includes a nurse call server that monitors inputs on GRS 232 and communicates relevant task and/or alert status changes to server 200 which, in turn, sends messages to badge 10 and mobile device 160 to change their respective task and alert lists, for example.

The present disclosure also contemplates that some user inputs, including voice inputs, on badges 10 and/or mobile device 160 alters the task and alert status, or other information, on display 240 of GRS 232. Thus, relevant user inputs on badges 10 and/or mobile devices 160 are communicated through the infrastructure of system 100, including the nurse call server, to GRS 232. Furthermore, the detection of badge 10 in a particular room by the RTLS portion of system 100 results in changes to the tasks and/or alerts shown on display 240 of GRS 232 in some embodiments. For example, the RTLS and the nurse call server may cooperate to determine that badge 10 of the caregiver assigned to a particular room is present in the room for a threshold amount of time (e.g., 1 minute, 2 minutes, or 5 minutes, just to give a few arbitrary time thresholds), then completion of a round and/or patient turn is automatically considered to have occurred and the nurse call server signals GRS 232 to change the rounding task status displayed thereon. The present disclosure also contemplates that, in response to badge 10 entering into a room in which an audible alarm is sounding from medical equipment 164 coupled to the nurse call system (e.g., a patient bed, an infusion pump, etc.), which room entry is determined by the RTLS, the nurse call server sends a message to the medical equipment to silence the audible alarm.

Figure 7:
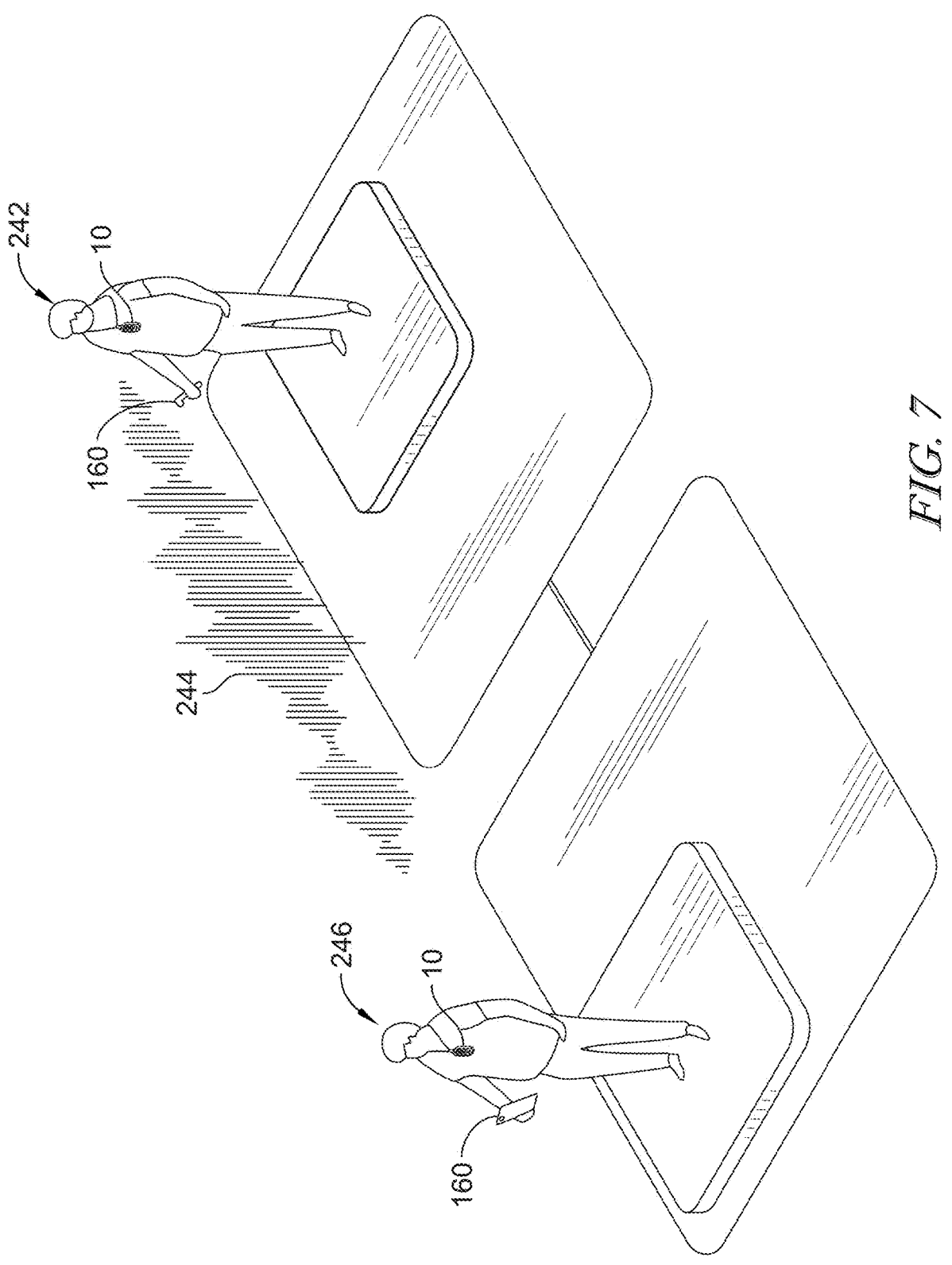
FIG. 7 is a diagrammatic view showing a first caregiver using a first communication badge for voice communications with a second communication badge of a second caregiver.
Figure 8:
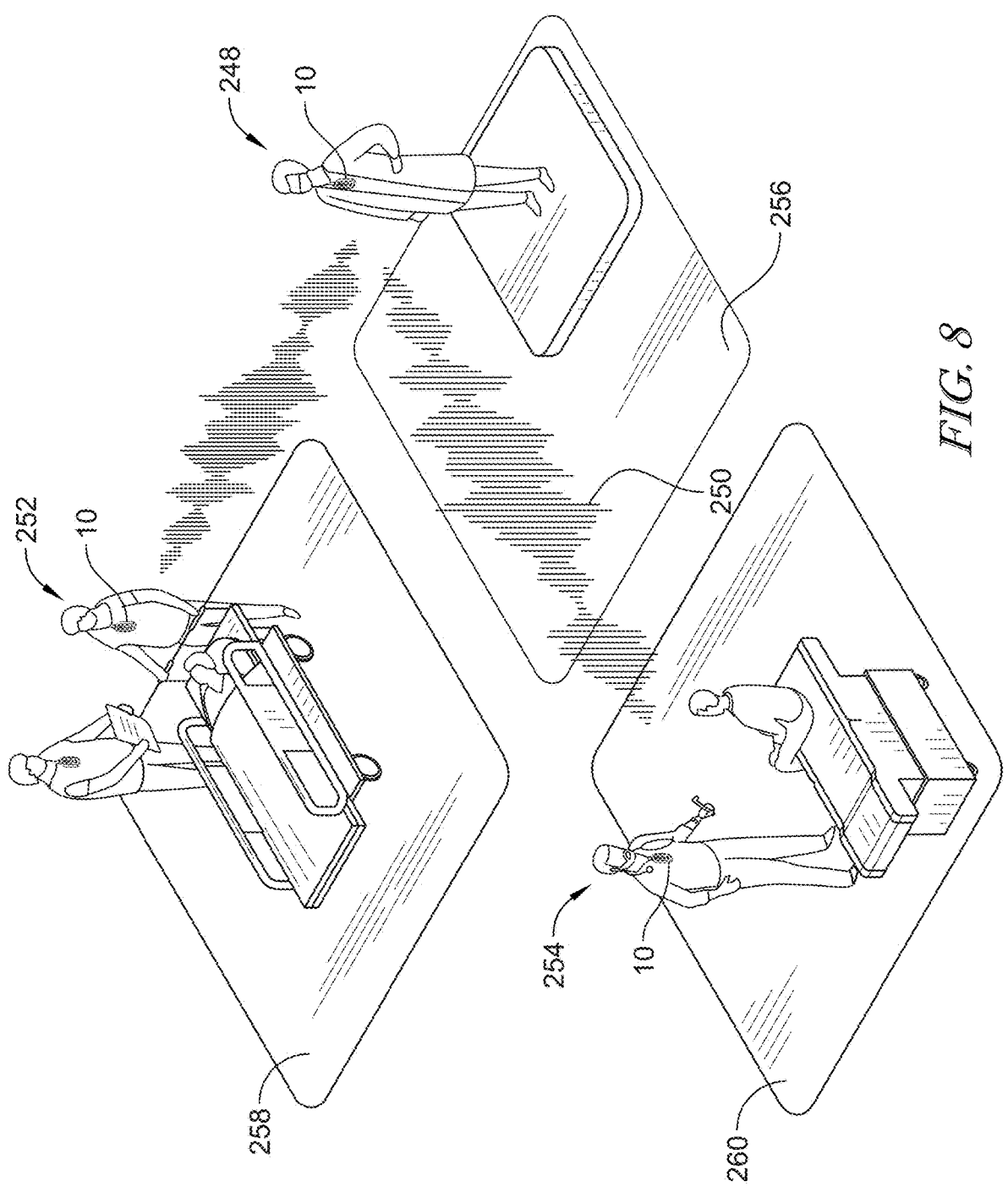
FIG. 8 is a diagrammatic view showing a doctor using a first communication badge to send a broadcast message to second and third communication badges worn by second and third caregivers, respectively.
Figure 9:
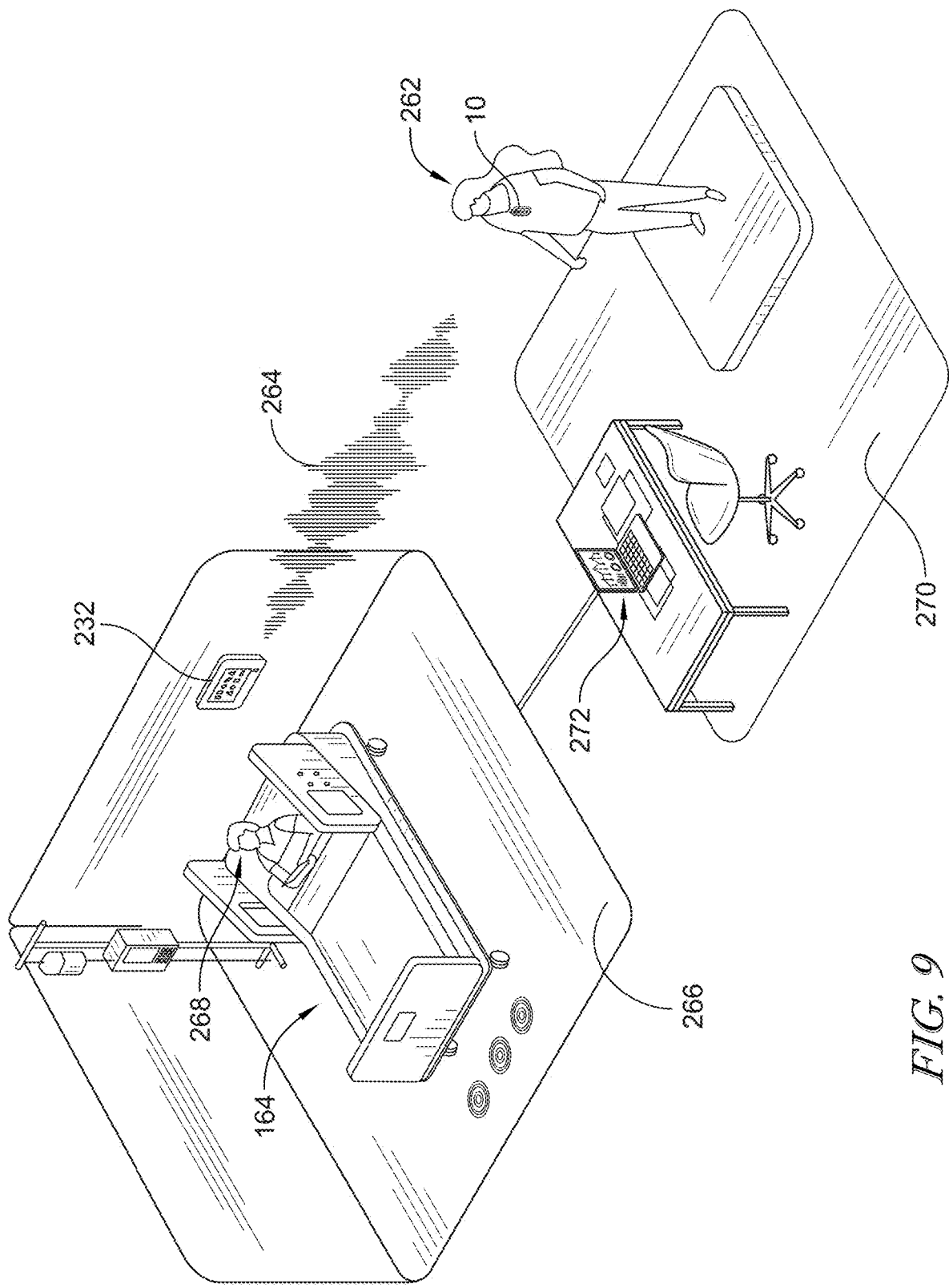
FIG. 9 is a diagrammatic view showing a caregiver using the communication badge of FIGS. 1-6 to engage in voice communications with a patient in a patient room through a graphical audio station located in the patient room.

Referring now to FIGS. 7-9, diagrammatic representations are provided to illustrate various functions of badge 10 that have been described hereinabove. In FIG. 7, for example, a first caregiver 242 uses communication badge 10 or mobile device 160 for voice communications over a communication link, indicated by diagrammatic waveform 244, with communication badge 10 or mobile device 160 of a second caregiver 246. The first caregiver 242 is depicted as also carrying a respective mobile device 160. Thus, caregivers 242, 246 are able to communicate with each other via any of a badge-to-badge, badge-to-phone, phone-to-badge, or phone-to-phone communication link 244 depending upon which of badge 10 and phone 160 is used by caregiver 242 to initiate the voice communications (e.g., place a call) and which of badge 10 and phone 160 is used by caregiver 246 to answer the call. If desired, caregiver 242 uses voice commands to place the call with their badge 10 and caregiver 246 uses voice commands to answer the call with their respective badge 10.

In FIG. 8, a doctor 248 uses his or her badge 10 to send a broadcast message, indicated by diagrammatic waveforms 250, to badges 10 of a first caregiver 252 and a second caregiver 254. Broadcast message 250 is transmitted simultaneously from badge 10 of the doctor 248 to the badges 10 of caregivers 252, 254. Furthermore, in the illustrative FIG. 8 example, the doctor 248 is located in a first room 256 of a healthcare facility, the first caregiver 252 is located in a second room 258 of the healthcare facility, and the second caregiver 254 is located in a third room 260 of the healthcare facility. Room 256 may be an office of the doctor 248, room 258 may be a patient room, and room 258 may be an examination room, for example. Therefore, by simultaneously sending broadcast message 250 to different caregivers 252, 254 in different rooms 258, 260 of the healthcare facility, the doctor does not need to contact the caregivers 252, 254 individually in separate calls to convey the information contained in the broadcast message 250.

According to the present disclosure, badge 10 is configurable to send a broadcast message for receipt by up to a predetermined number (e.g., 500) other badges 10. Embodiments in which mobile device 160 and other endpoints, such as those mentioned hereinabove, receive broadcast messages transmitted by badge 10 are also within the scope of the present disclosure. The broadcast message 250 is a pre-recorded message in some instances, is a pre-established text message in other instances, and is a spoken broadcast message in still other instances. Thus, the sender of the broadcast message, illustratively the doctor 248 in the FIG. 8 scenario, navigates the menu of badge 10 using voice inputs or buttons 58, 60, 62 to select whether the broadcast message is to be the pre-recorded voice message, pre-established text message, or to be spoken into the sender's badge 10 for substantially real-time transmission to the badges of a predetermined broadcast group of recipients. If the broadcast message is pre-recorded, then menu options of badge 10 are navigated to make a voice recording of the message prior to its transmission to the designated broadcast group.

Also according to the present disclosure, the broadcast group of recipients is chosen using voice inputs or buttons 58, 60, 62 of badge 10 of the broadcast sender, or is set up using an administration computer such as a computer of portal 222, or is set up in a nurse call system computer, an ADT system computer, an EMR system computer, or some other computer. Alternatively or additionally, mobile device 160 is operable to establish a broadcast group of recipients. Regardless of how the broadcast group of recipients is set up, the present disclosure contemplates that a name is designated for the group and then, the broadcast sender refers to the given name (e.g., code blue team, surgical team A, surgical team B, ICU team, nurse group 1, nurse group 2, therapist group, MA's in L&D unit, etc.) to identify the badges 10, mobile devices 160, and other enpoints of the group of recipients to which the broadcast message 250 is to be transmitted from the badge 10 of the broadcast sender. Such broadcast groups, once established, are stored in directory 204 of server 200, for example.

Referring now to FIG. 9, a caregiver 262 uses communication badge 10 for voice communications over a communication link, indicated by diagrammatic waveform 264, with GRS 232 in a patient room 266. A patient 268 supported on patient bed 164 has placed a nurse call by pressing a nurse call button of patient bed 164 in the illustrative example, but bed 164 does not have any microphone or speaker with which to communicate with any caregivers answering the nurse call. Thus, in the illustrative scenario, when badge 10 of caregiver 262 is used to answer the nurse call, the communications with patient 268 occurs via a microphone and speaker of GRS 232. Also in the illustrative example, caregiver 262 is located at a master nurse station 270 which has a master nurse station console or computer 272.

Master nurse station computer 272 and GRS 232 of FIG. 9 are both communicatively coupled with a nurse call server (not shown) of the corresponding nurse call system as is known in the art. The nurse call server determines the end point device (e.g., patient bed 164 or pillow speaker unit) that the patient used to place the nurse call and also determines whether the patient bed 164 is equipped with a speaker and microphone. Based on this information in the nurse call server of the nurse call system, the nurse call server is able to determine whether the communication link 264 from badge 10 of the responding caregiver should be made with the patient bed 164, the pillow speaker unit, or the GRS 232.

Based on the foregoing, therefore, if the patient presses a nurse call button on a bed 164 that is equipped with a speaker and a microphone (or a bed 164 that has a speaker that also serves as a microphone), then communication link 264 is established between badge 10 of the responding caregiver, such as caregiver 262 in the illustrative FIG. 9 example, and the patient bed 164. If the patient presses a nurse call button on a pillow speaker unit having a speaker and a microphone, then communication link 264 is established between badge 10 of the responding caregiver and the pillow speaker unit. Otherwise, if there is no bed 164 or pillow speaker unit with a speaker and microphone from which the nurse call originated, then communication link 264 is established between badge 10 of the responding caregiver and the GRS 232 in the room from which the nurse call originated, as depicted diagrammatically in FIG. 9.

The present disclosure further contemplates that mobile device 160 of a responding caregiver may be used to establish communication link 264 to respond to a nurse call in lieu of badge 10. In some embodiments of system 100, after the caregiver speaks with the patient placing the nurse call using their badge 10 or mobile device 160, the nurse call system clears the nurse call from being an active call to which a response is required. A list of such active calls may appear on the display of master nurse station computer 272 and/or on a status board at the master nurse station 270 and/or on any GRS 232 in any patient room. Once a particular call is cleared in the nurse call system, it is removed from the lists of active (aka unanswered) nurse calls on each of the display of computer 272, the status board, and the GRS 232. Also, the cleared call also is removed from any lists and no longer appears that are viewable on any badges 10 or mobile devices 160.

Figure 10:
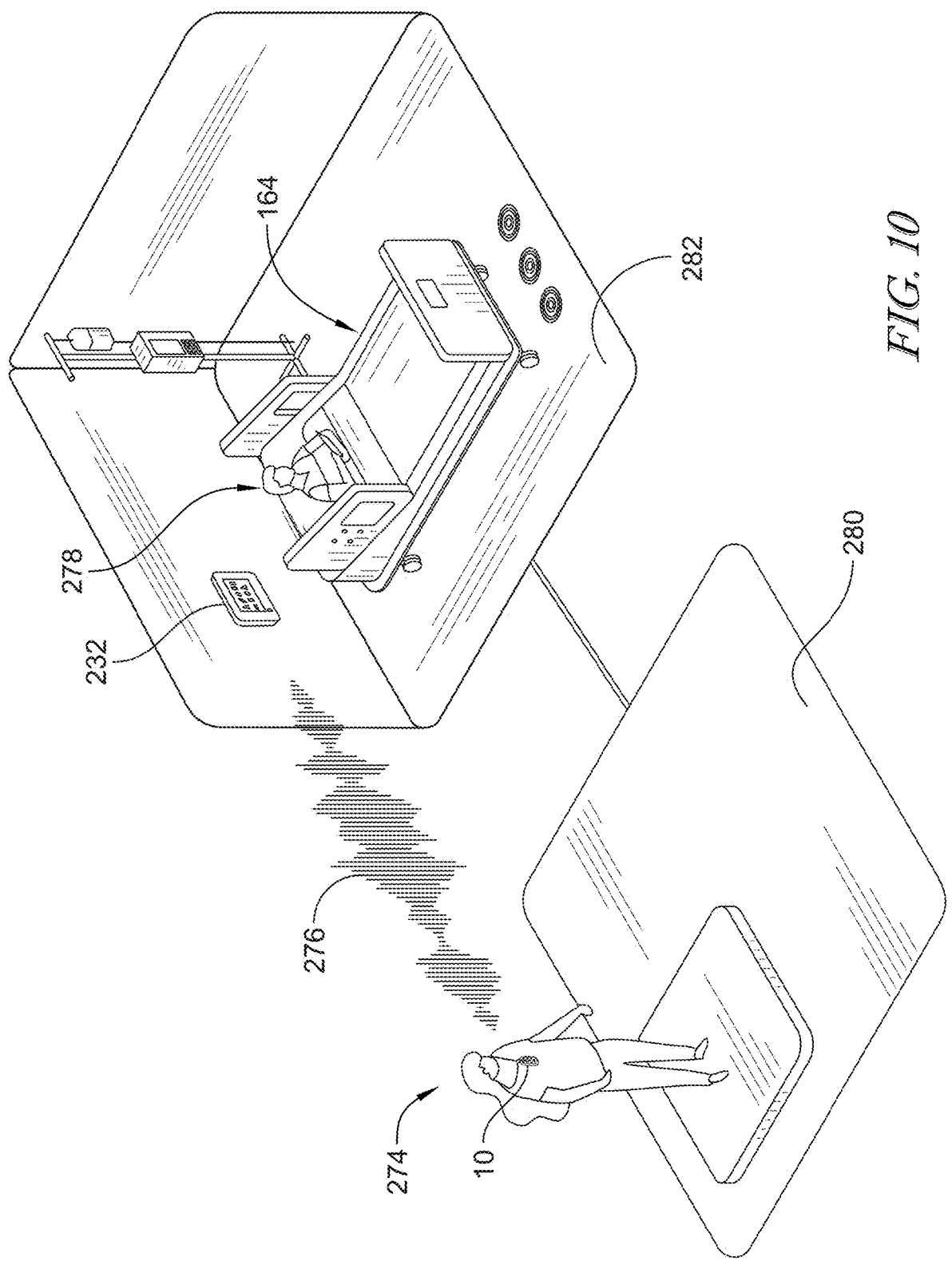
FIG. 10 is a diagrammatic view showing a caregiver using the communication badge of FIGS. 1-6 to control a function of a patient bed located in a patient room by using voice commands that are received by a nurse call system and converted to bed control commands that are transmitted to the patient bed.

Referring now to FIG. 10, a caregiver 274 uses communication badge 10 for sending a voice command over a communication link, indicated by diagrammatic waveform 276, via the nurse call system that includes GRS 232 to the associated patient bed 164 to turn on, or turn off, a designated function of the bed 164 which supports a patient 278. In the illustrative example, caregiver 274 is located in a first patient room 280 and the patient bed 164 being controlled with the voice command from badge 10 of caregiver 274 is located in a second patient room 282. Thus, the voice command(s) sent over communication link 276 is/are received by the nurse call system and converted to bed control commands that are transmitted to the patient bed 164 via the nurse call system equipment.

The present disclosure contemplates that badge 10 is usable by the caregiver 274 to control any function of bed 164 when the caregiver 274 is located in the same room 282 with bed 278, but that when the caregiver 274 is located outside of the room 282, only a limited set of bed functions are controllable with voice commands or button presses using the corresponding badge 10 of the caregiver 274. Thus, the nurse call system relies on locating information from RTLS to determine the location of the caregiver 274 when voice commands and/or button presses are provided by the caregiver 274 using badge 10 to control the bed 164 in a particular room, such as the room 282 in the illustrative example. For example, in some embodiments, if the caregiver 274 is present in the room 282, then bed movement functions such as raising, lowering, and/or tilting an upper frame of bed 164 relative to a base frame, and raising or lowering articulating mattress support deck section of bed 164, can be operated with voice commands through badge 10 or button presses on badge 10. Such movements of bed 164 are permitted using badge 10 under these circumstances because caregiver 274 is in the room 282 and can observe the bed movements directly to confirm their safety. However, when caregiver 274 is outside of the room 282, such bed movements using badge 10 are not permitted by system 100. Another function of bed 164 that may be controllable using badge 10 only when caregiver 272 is in the room 282 with bed 164 is electrical braking and releasing (aka unbraking) of casters of bed 164.

As an example of a function that can be controlled using voice commands or button presses of badge 10 when the caregiver 274 is located outside of the room 282 as well as inside the room 282, is turning on or turning off a bed monitoring protocol, such as a falls risk protocol of bed 164. Suitable voice commands in this regard include, for example, "hey Scotty, turn on the Patient Safety Protocol for the bed in room [room number]," "hey Scotty, turn on the Falls Protocol for the bed in room [room number]," "hey Scotty, turn off the Patient Safety Protocol for the bed in room [room number]," and "hey Scotty, turn off the Falls Protocol for the bed in room [room number]." Similar menu commands are provided on display 46 of badge 10 when buttons 58, 60, 62 are used to navigate the available menu of badge 10.

According to one example of the falls risk protocol, the upper frame of bed 164 should be in a lowered position relative to the base fame, one or more siderails of bed 164 should be in their respective raised positions to block patient 278 from egressing from bed 164, and a bed exit/patient position monitoring (PPM) system of bed 164 should be enabled to monitor the position of patient 278 on bed 164 and generate an alert if patient 278 moves toward exiting bed 164 by a threshold amount. If any one or more of the falls risk protocol conditions is violated, then a local audible alarm on bed 164 will sound and an alert message to the nurse call system will be sent from bed 164 for promulgation to badges 10 and mobile devices 160 of assigned caregivers, as well as for display on GRS's 232, master nurse station computers 272, status boards of the nurse call system, and illumination of a dome light located outside of the corresponding patient room 282.

Some patient beds 164 have bed exit/PPM systems that operate at different levels of sensitivity (e.g., two or three or more levels of sensitivity) which are selectable. Such bed exit/PPM system use load cells of a weigh scale system of the bed to also determine the position of the patient. In this regard, some beds 164 have three bed exit/PPM modes including a patient movement mode, a patient positioning mode, and a bed exiting mode. The patient movement mode is the most sensitive and results in an alarm if the bed exit/PPM system of bed 164 detects a small amount of patient movement such as the patient sitting up in bed 164 or rolling over toward one side of bed 164 of the other. The patient positioning mode is an intermediate mode that results in an alarm if the bed exit/PPM system of bed 164 detects a patient moving close to the side edge bed 164 in preparation for potentially exiting the bed 12. The exiting mode is the least sensitive mode and results in an alarm if the bed exit/PPM system of bed 164 detects that the patient has moved all the way to the side edge of the bed 164 or has transferred some of their weight off of the bed 164 during the process of exiting the bed 164.

With the foregoing in mind, it is contemplated that voice commands provided to badge 10 or the button presses on badge 10 can be used to select at which level of sensitivity the Patient Safety Protocol (aka Falls Protocol) is to operate when turned on. Similarly, patient bed 164 has multiple siderails, such as having four siderails including a left head end siderail, a right head end siderail, a left intermediate siderail, and a right intermediate siderail. Badge 10 is also able to receive voice commands and/or button presses to select which one, two, three, or four of these siderails must be in respective raised positions to be considered in compliance with the Patient Safety Protocol (aka Falls Protocol). Thus, not only is badge 10 usable to receive voice commands and/or button presses to turn the falls risk protocol on and off, badge 10 is also usable to receive voice commands and/or button presses to program the conditions of bed 164 that must be met according to the falls risk protocol. Such falls risk programming can also be done using inputs on bed 164 and at one or more other computers of system 100 such as the master nurse station computer 272 according to the present disclosure.

In some embodiments of system 100, another function that can be voice commanded using badge 10 when the caregiver 274 is located outside of the room 282 as well as inside of the room 282, is turning on and turning off a heart rate and/or respiration rate monitoring function of bed 164. For example, some embodiments of patient bed 164 include a heart rate (HR) and/or respiration rate (RR) sensor located on a head section (aka a back section or torso section) of a mattress support deck beneath the torso supporting portion of the mattress supported by the head section. Such a suitable HR/RR sensor is the contact free, continuous monitoring (CFCM) sensor of the CENTRELLA® Smart+ Bed available from the Hill-Rom Company, Inc. subsidiary of Baxter International, Inc. For additional details of the CENTRELLA® Smart+ Bed, see U.S. Pat. No. 10,517,784 which is hereby incorporated by reference herein to the extent not inconsistent with the present disclosure which shall control as to any inconsistencies. Suitable voice commands in this regard include, for example, "hey Scotty, turn on CFCM for the bed in room [room number]," "hey Scotty, turn on vitals monitoring for the bed in room [room number]," "hey Scotty, turn off CFCM for the bed in room [room number]," and "hey Scotty, turn off vitals monitoring for the bed in room [room number]."

In some embodiments, a mattress and associated pneumatic system of bed 164 are operable to provide one or more therapies or other functions to the patient 278 supported thereon. Such mattress-based therapies and functions include, for example, a turn assist function, continuous lateral rotation therapy (CLRT), alternating pressure (AP) therapy, microclimate management (MCM) therapy, percussion and vibration (P&V) therapy, and a heel relief function. It is contemplated that any of these mattress-based therapies and functions can be turned on and off via corresponding button presses or voice commands entered into badge 10 and communicated to bed 164 via the nurse call system.

In some embodiments, the caregiver must be present in the room 282 with bed 164 when providing such voice commands or button presses on badge 10 to control mattress-based therapies and functions. In other embodiments, the caregiver can provide such voice commands and button presses on badge 10 to control mattress-based therapies and functions of bed 164 when either inside or outside of the room 282 in which bed 164 is located. In still other embodiments, some mattress-based therapies can only be turned on and off using voice commands or button presses on badge 10 when the caregiver is located in the room 282 with bed 164 and others of the mattress-based therapies can be turned on and off using badge 10 when the caregiver is inside or outside of the patient room 282 in which bed 164 is located. For example, badge 10 may be required to be in the room 282 to control the turn assist function and the CLRT of bed 164 but may be able to control all of the other mattress-based therapies and functions of bed 164 regardless of whether inside or outside of the room 282, just to give one scenario.

Based on the foregoing, it will be appreciated that the primary component of system 100 is, in some embodiments, the wearable locating and communication badge 10 which interfaces with e.g., a cloud-based voice assistant 186 that employs e.g., an LLM with RAG, in response to a spoken key word, "Scotty" in the illustrative example. Thus, badges 10 of system 100 empower care team members in healthcare environments with hands-free workflows and communication. Voice commands and/or buttons 56, 58, 60, 62, 64 of badge 10 are available to initiate a call to a fellow staff member or accept an incoming call from any communication device controlled by the clinical facility (e.g., desk phones or other hard wired phones; mobile devices 160 including mobile phones, tablet computers, laptop computers, and/or computer-on-wheels (COW); other badges 10; and/or nurse call communication devices (e.g., room stations; master stations; staff stations; handheld pillow speakers units; and/or hospital beds with nurse call functionality such as nurse call buttons, speakers, and/or microphones)). Badge 10 also has a broadcast feature, initiated by a spoken broadcast command or by pressing one or more of buttons 56, 58, 60, 62 in some embodiments, which sends a short user-recorded message to a selection of other badges 10.

Badge 10 further has a dedicated button 64 that offers versatile functionality. When set for speed dial, this button 64 initiates an outgoing call to one or more pre-defined communication endpoints. Thus, button 64 is programmed as a duress button in some implementations. When system 100 is configured for integration with third-party systems, such as nurse call systems, badge 10 operates to report button press activity that is used for additional workflows. For example, if badge 10 is used to report that a round has been completed for a particular patient, then a next round for the patient is scheduled within system 100. As another example, if badge 10 is used to report that a patient room has been cleaned after a patient discharge, then system 100 operates to designate the patient room as being available for a new patient admission (e.g., within an admission, discharge, and transfer (ADT) system of system 100). In some embodiments, badge 10 also provides reliable and near real-time, x-y coordinate locating data for wearers when enabled and integrated with a supported RTLS.

With regard to the voice-activated workflows just mentioned, one or more voice inputs into badge 10 are processed by cloud-based assistant 186 having LLM with RAG and corresponding messages returned to another connected system, such as a nurse call system, which in turn sets up tasks (e.g., rounding, patient turn, room cleaning, etc.) for staff members to execute. Thus, caregivers with badges 10 use hands free voice commands to initiate routines (e.g., task workflows) in the nurse call system. In this regard, caregivers set rounding reminders, indicate that certain tasks (e.g., patient turns) have started, indicate that certain tasks (e.g., replacement of an IV fluid bag) have been completed, or set up patient protocols (e.g., sepsis response protocols) using one or more spoken commands rather than going to a console, such as GRS 232, master nurse station 272, staff station, or other physical interface to complete these same types of inputs manually.

In some embodiments, the workflows are constrained by rules such as specific task entries into system 100 are limited by privileges such as caregiver role, patient assignments, or physical location as determined by the RTLS of system 100. The present disclosure also contemplates that use of wake words, or pressing push-to-talk button 56, is replaced by ambient monitoring with microphones 48 listening on an ongoing basis such that assistant 186 recognizes the occurrence of workflow inputs based on natural language processing (NLP) with corresponding tasks and reminders being offered to the corresponding caregiver the respective badge 10 and/or being automatically established within system 100 based on the ambient conversations analyzed and the rules associated therewith.

In some embodiments, voice inputs or button presses on badge 10, are used to turn the ambient listening function of badge 10 on and off. Alternatively or additionally, the ambient listening function of badge 10 is turned on and off based on the caregiver's location in the healthcare facility as detected by the RTLS of system 100. For example, the ambient listening function of badge 10 is turned on when the caregiver transporting badge 10 is located in a patient room of an assigned patient or is located at the bedside (e.g., within a threshold distance of the patient bed) of an assigned patient. Further alternatively or additionally, the ambient listening function of badge 10 is turned on and off based on a presence or proximity of a co-located care team member. For example, if one caregiver is within proximity of another caregiver (e.g., within a threshold distance such as three feet or ten feet just to give a couple arbitrary examples) the listening function of the badges 10 of either or both of the caregivers is turned on. If none of the conditions for turning on the ambient listening function of badge 10 is met, then the listening function is turned off.

In some embodiments, badge 10 is also configured with a speed dial number that is called, or an alert message to the nurse call system, in the event of a button press failure. In this regard, a button press failure is considered to occur when any of buttons 56, 58, 60, 62 of badge 10 is pressed to illicit a response from system 100, but another portion of system 100, particularly servers of blocks 170, 172, 186 of system 100, does not respond back with any response to indicate a successful communication of the button press event. Thus, badge 10 initiates a speed dial to a designated number and/or sends a button press failure message to the nurse call system as an alert and the nurse call system, in turn, annunciates the alert within the nurse call system and/or on one or more mobile devices in a programmed manner. In some embodiments, the button press failure alert is first sent from badge 10 to the nurse call system and if an acknowledgement or confirmation is not received by badge 10 from the nurse call system, then the badge 10 calls the speed dial number as a back-up.

The present disclosure further contemplates that badge 10 is configured to receive and respond to secondary notifications of alerts from an integrated alert management system. Medical devices 164 such as infusion pumps, vital signs monitors, and other patient care equipment, provide primary alerts to an alert management server of such an alert management system, for example. Secondary notification responses from badge 10 (e.g., to acknowledge responsibility for responding to such secondary alerts) may not address or clear the primary notification from the alert management system, but such possibilities are not intended to be ruled out.

Badges 10 of system 100 and the cloud-based assistant 186 also interfaces or integrates with a supported hospital communication and information management system such as the system represented by one or more of blocks 170, 200, 218 in FIG. 5. This integration allows access to user-associated information (e.g., roles and teams) and supports call routing (e.g., via a PBX system). To manage security features such as credentials, authentication sources, and user role and privilege assignments, system 100 includes a supported centralized management system such as the Digital Health Gateway available from Baxter International, Inc. of Deerfield, IL, U.S.A. in some embodiments.

Further according to the present disclosure, badge 10 is used for voice entry of caregiver notes and dictation. Such notes and dictation can be recorded as sound files or can be converted to text for storage, or both, at the option of the caregiver operating badge 10. Accordingly, a notes option and a dictation option are among the options to which the caregiver can navigate on the menu of badge 10 using buttons 56, 58, 60, 62 or voice commands, in some embodiments. Once created, the notes and dictation files are stored in memory 76 and/or in memory of MCU 72 for playback through speaker 52 of badge 10 or for viewing on display 46 of badge 46. In some embodiments, the notes and dictation files are also retrievable for viewing or listening using the associated mobile device 160 of the caregiver. In this regard, copies of the notes and/or dictation files are stored in memory of the associated mobile device 160 after creation on badge 10 and transmission to mobile device 160.

In some embodiments, system 100 includes one or more charging stations of the type depicted in U.S. Design application Ser. No. 29/938,898, filed Apr. 24, 2024, and titled "Docking Station," which is hereby incorporated by reference herein. Each charging station charges and stores replaceable batteries 43 when not in use with any of badges 10. Up to four charging stations may be daisy chained from the same power outlet and are either desk or wall mountable. Each docking or charging station is configured to store and charge up to eight batteries 43.

A web application, stored and operated on portal 222, is provided in some embodiments to configure badges 10 of system 10 and also to manage the directory 204, badges 10, user accounts, and device associations (e.g., badge-to-caregiver associations, badge-to-mobile device associations, etc.) for a given facility. Portal 222 includes an administration computer that receives inputs from administrators or other authorized users in this regard to set up the desired associations, for example.

By way of recap, badge 10 has a number of features and functions including the following:

Login/Logout;

Handsfree wake up (e.g., use of "Scotty" as key word);

Place a call by voice to another badge 10 by staff name, multiple name matches, nicknames or preferred names or by assignments (locations and roles provided by a nurse call system);

Accept or decline responsibility for responding to incoming alerts using badge 10 via voice commands or button presses;

Receive nurse call alerts and call back into the room form which the nurse call alert originated;

Place a configurable nurse call by button press on badge 10;

Call cancelation based on staff location as determined from badge 10 communication (e.g., UWB transmissions) with an RTLS;

Display locations of badges 10 on a nurse call and/or precision locating map of an RTLS;

Send a broadcast message to other communication devices (e.g., other badges 10, mobile devices 160, hardwired telephones, pagers, audio stations of a nurse call system, master stations of a nurse call system, staff stations of a nurse call system, and/or pillow speaker units);

Enter into a do-not-disturb (DND) mode;

Auditing exports from portal 222;

Device management, status, and metrics within portal 222;

Facility management within portal 222 (configuration, device registration/deregistration, staff and non-staff contacts for badge 10);

Firmware updates to badges 10 from portal 222;

Voice duress input to badge 10;

Back-up speed dial to designated endpoint(s) upon button press failure;

Voice commands to turn on/off patient safety protocol of hospital bed (e.g., falls risk protocol being on requires (i) designated siderails to be in raised positions, (ii) upper frame of bed to be in lowered position relative to base frame of bed, and (iii) bed exit/patient position monitoring (PPM) system of bed to be enabled so as to alarm if patient moves toward exiting the bed by a threshold amount); and Badge 10 also used as a locating badge for an RTLS system so that badge location displayed on a floor plan or other healthcare facility map on a display of the RTLS.

The present disclosure further contemplates methods of making and/or using system 100, including badge 10. Methods of voice communication by caregivers using system 100, including badge 10, are also contemplated. The present disclosure further contemplates, one or more tangible computer-readable storage media including a plurality of instructions that, when executed, cause any one or more of the functions of system 100, including badge 10, to be carried out. Thus, the description herein of system 100, including badge 10, is also applicable to methods thereof and one or more tangible computer-readable storage media used to implement the functions thereof.

When the terms "is" or "has" or "includes" or the like are used hereinabove, they are all intended to be synonymous and mean that, in the spirit of all illustrative embodiments herein, the thing recited is optional and may or may not be required to be present in the respective embodiment or in other embodiments. Furthermore, while the embodiments herein are presented in the context of a healthcare communication system, the present disclosure contemplates that the same or similar embodiments can be deployed in other environments where wearable communication is desired.

When terms of degree such as "generally," "substantially," and "about" are used herein in connection with a numerical value or a qualitative term susceptible to a numerical measurement, it is contemplated that an amount that is plus or minus 10 percent, and possibly up to plus or minus 20 percent, of the numerical value, is covered by such language, unless specifically noted otherwise, to at least account for manufacturing tolerances. Otherwise, a suitable definition for the terms "generally," "substantially," and "about," is largely, but not necessarily wholly, the term specified.

When the terms "a" or "an" or the phrases "one or more" or "at least one" are used herein, including in the claims, they are all intended to be synonymous and mean that one, or more than one, of the thing recited may be present. Similarly, when the phrases "a plurality" or "two or more" or "at least two" or "a pair" are used, they are all intended to be synonymous and mean that two, or more than two, of the thing recited may be present. Furthermore, when the language "at least a portion" and/or "a portion" is used herein, the item can include a portion and/or the entire item unless specifically stated to the contrary.

According to this disclosure, phrases of the form "at least one of A and B" and "at least one of the following: A and B" and similar such phrases, mean "A alone, or B alone, or both A and B." Phrases of the form "at least one of A or B" and "at least one of the following: A or B" and similar such phrases, also mean "A alone, or B alone, or both A and B." Furthermore, phrases of the form "A and/or B" also mean "A alone, or B alone, or both A and B."

Although certain illustrative embodiments have been described in detail above, variations and modifications exist within the scope and spirit of this disclosure as described and as defined in the following claims.

The invention claimed is:

1. A healthcare communicator comprising:

a voice communication badge including a housing configured to be worn by a caregiver, a controller carried by the housing, a display coupled to the controller and visible on the housing, a microphone coupled to the controller and configured to detect a caregiver's spoken commands, at least one user input carried by the housing, wherein the at least one user input is usable by the caregiver to select or alter first information appearing on the display, a speaker coupled to the controller and configured to provide audio outputs, a wireless module carried by the housing and coupled to the controller, the wireless module being configured to send at least one of long range signals and short range signals, a location module coupled to the controller and configured to emit or receive beacon signals that are communicated with a real-time locating system (RTLS) having a locating computer configured to determine a location of the voice communication badge in the healthcare facility based on the beacon signals, and a pairing module communicatively coupled with a software application installed on a mobile phone of the caregiver, wherein selection of an input of the mobile phone selects or alters the first information appearing on the display of the voice communication badge, wherein the at least one user input further comprises a plurality of buttons carried by the housing and coupled to the controller, and wherein the controller and the wireless module cooperate to send a control message to a medical device to control a function of the medical device in response to a device voice command received by the microphone or in response to use of one or more of the plurality of buttons to navigate to a device control option on a menu appearing on the display, wherein the medical device comprises a patient bed and wherein the control message results in a falls risk protocol of the patient bed being turned on or turned off, wherein the falls risk protocol, when turned on, monitors bed status to assure that one or more siderails of the patient bed are in respective raised positions, an upper frame of the patient bed is in a lowered position relative to a base frame of the patient bed, and that a bed exit/patient position monitoring (PPM) system of the patient bed is enabled to determine a position of a patient on the patient bed.

2. The healthcare communicator of claim 1, wherein the wireless module and the pairing module are integrated together into a common module.

3. The healthcare communicator of claim 1, wherein the controller and the wireless module cooperate to send a broadcast message to a plurality of endpoint devices of a broadcast message group of recipients in response to a broadcast voice command received by the microphone or in response to use of one or more of the plurality of buttons to navigate to a broadcast transmission option on a menu appearing on the display.

4. The healthcare communicator of claim 3, wherein the broadcast message comprises any one or more of the following: a pre-recorded voice message, a pre-established text message, and a voice message spoken in real time by a user.

5. The healthcare communicator of claim 3, wherein the broadcast message group is configurable by use of the mobile phone or by use of a remote computer.

6. The healthcare communicator of claim 3, wherein the broadcast message group is stored in a directory of a server along with other broadcast message groups.

7. The healthcare communicator of claim 3, wherein at least some of the plurality of endpoints to which the broadcast message is sent comprise other healthcare communicators of the broadcast message group and/or other mobile phones of the broadcast message group and/or communication devices of a nurse call system.

8. The healthcare communicator of claim 7, wherein the communication devices of the nurse call system include any one or more of the following: a master nurse station console, a graphical room station (GRS), a graphical staff station (GSS), a pillow speaker unit, and the patient bed.

9. The healthcare communicator of claim 1, wherein selection of the at least one user input of the voice communication badge selects or alters second information appearing on the mobile phone.

10. The healthcare communicator of claim 1, wherein the control command results in a vital signs monitoring function of the patient bed being turned on or turned off.

11. The healthcare communicator of claim 1, wherein the control command is able to control any function from among a plurality of functions of the patient bed when the healthcare communicator is located in a patient room with patient bed, and wherein, if the healthcare communicator is located outside of the patient room in which the patient bed is located, the control command is only able to control a limited set of bed functions from among the plurality of bed functions.

12. The healthcare communicator of claim 1, wherein at least one button of the plurality of buttons is operable as a duress button which, in response to being pressed, causes the controller to speed dial and/or send a duress message via the wireless module to one or more programmed recipients.

13. The healthcare communicator of claim 12, wherein receipt of a spoken duress command by the microphone causes the controller to speed dial and/or send the duress message via the wireless module to the one or more programmed recipients.

14. The healthcare communicator of claim 1, wherein the healthcare communicator is configured to receive a nurse call from a nurse call system having a plurality of devices from which the nurse call may originate, and wherein the healthcare communicator is configured to permit a user to answer the nurse call by forming a voice communication link with a device of the plurality of devices from which the nurse call originated.

15. The healthcare communicator of claim 1, wherein the pairing module is communicatively coupled with the software application installed on the mobile phone via network infrastructure of a healthcare facility and/or via a cloud-based voice assistant server having a large language model (LLM) with retrieval augmented generation (RAG).

16. A healthcare communication method for a healthcare facility, the healthcare communication method comprising:

providing a voice communication badge to a caregiver, the voice communication badge including a housing, a controller carried by the housing, a display coupled to the controller and visible to the caregiver, a microphone coupled to the controller and configured to detect the caregiver's spoken commands, a plurality of user inputs carried by the housing, a speaker coupled to the controller and configured to provide audio outputs, a wireless communication module carried by the housing and coupled to the controller, and a location module coupled to the controller, wherein the plurality of user inputs comprises a plurality of buttons carried by the housing and coupled to the controller;

sending and receiving, with the wireless communication module of the voice communication badge, long range wireless signals and short range wireless signals;

emitting, with a location module of the voice communication badge, beacon signals that are received by at least one receiver of a real-time locating system (RTLS);

determining, with a locating computer, a location of the voice communication badge in the healthcare facility based on the beacon signals;

associating a mobile phone of the caregiver with the voice communication badge;

using, after the voice communication badge and the mobile phone are associated, the at least one user input to select or alter first information appearing on the display of the voice communication badge which results in also selecting or altering, respectively, second information appearing on the mobile phone, and/or using, after the voice communication badge and the mobile phone are associated, an input field shown on the mobile phone which results in selecting or altering third information appearing on the display of the voice communication badge; and operating the controller and the wireless module to cooperate to send a control message to a medical device to control a function of the medical device in response to a device voice command received by the microphone or in response to use of one or more of the plurality of buttons to navigate to a device control option on a menu appearing on the display;

wherein the medical device comprises a patient bed and wherein the control message results in a falls risk protocol of the patient bed being turned on or turned off; and wherein the falls risk protocol, when turned on, monitors bed status to assure that one or more siderails of the patient bed are in respective raised positions, an upper frame of the patient bed is in a lowered position relative to a base frame of the patient bed, and that a bed exit/patient position monitoring (PPM) system of the patient bed is enabled to determine a position of a patient on the patient bed.

17. One or more tangible computer-readable storage media comprising a plurality of instructions that, when executed, cause a healthcare communication system to:

send from a wireless communication module of a voice communication badge of a caregiver, long range wireless signals and short range wireless signals;

emit from a location module of the circuitry of the voice communication badge, beacon signals that are received by at least one receiver of a real-time locating system (RTLS);

determine, with a locating computer, a location of the voice communication badge in the healthcare facility based on the beacon signals;

associate a mobile phone of the caregiver with the voice communication badge;

after the voice communication badge and the mobile phone are associated, receive at least one user input at the voice communication badge to select or alter first information appearing on a display of the voice communication badge which results in also selecting or altering, respectively, second information appearing on the mobile phone, and/or, after the voice communication badge and the mobile phone are associated, receive a selection on an input field shown on the mobile phone which results in selecting or altering third information appearing on the display of the voice communication badge; and operate a controller of the voice communication badge and the wireless communication module to send a control message to a medical device to control a function of the medical device in response to a device voice command received by a microphone of the voice communication badge or in response to use of one or more of a plurality of buttons carried by the housing and coupled to the controller to navigate to a device control option on a menu appearing on the display of the voice communication badge;

wherein the medical device comprises a patient bed and wherein the control message results in a falls risk protocol of the patient bed being turned on or turned off;

wherein the falls risk protocol, when turned on, monitors bed status to assure that one or more siderails of the patient bed are in respective raised positions, an upper frame of the patient bed is in a lowered position relative to a base frame of the patient bed, and that a bed exit/patient position monitoring (PPM) system of the patient bed is enabled to determine a position of a patient on the patient bed.

* * * * *